United States Patent
Harris et al.

(10) Patent No.: US 9,506,046 B2
(45) Date of Patent: Nov. 29, 2016

(54) POLYPEPTIDES HAVING AMYLOLYTIC ENHANCING ACTIVITY AND POLYNUCLEOTIDES ENCODING SAME

(75) Inventors: Paul Harris, Carnation, WA (US); Mark Wogulis, Davis, CA (US)

(73) Assignee: Novozymes, Inc., Davis, CA (US)

( * ) Notice: Subject to any disclaimer, the term of this patent is extended or adjusted under 35 U.S.C. 154(b) by 580 days.

(21) Appl. No.: 13/130,417

(22) PCT Filed: Nov. 2, 2009

(86) PCT No.: PCT/US2009/062955
§ 371 (c)(1),
(2), (4) Date: Jul. 25, 2011

(87) PCT Pub. No.: WO2010/059413
PCT Pub. Date: May 27, 2010

(65) Prior Publication Data
US 2011/0283421 A1    Nov. 17, 2011

Related U.S. Application Data

(60) Provisional application No. 61/120,617, filed on Dec. 8, 2009, provisional application No. 61/116,605, filed on Nov. 20, 2008.

(51) Int. Cl.
| | | |
|---|---|---|
| C11D 3/386 | (2006.01) | |
| C12N 1/20 | (2006.01) | |
| C12P 19/16 | (2006.01) | |
| C12N 9/26 | (2006.01) | |

(52) U.S. Cl.
CPC ..... *C12N 9/2414* (2013.01); *C12Y 302/01001* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 8,343,747 B2 * | 1/2013 | Burke et al. | 435/205 |
| 2007/0157329 A1 * | 7/2007 | Callen et al. | 800/18 |
| 2009/0119022 A1 * | 5/2009 | Timberlake et al. | 702/20 |

FOREIGN PATENT DOCUMENTS

| | | | | |
|---|---|---|---|---|
| EP | 2772545 A1 * | 9/2014 | | C12P 19/00 |
| WO | WO 2004/091544 | 10/2004 | | |
| WO | 2008/080093 A2 | 7/2008 | | |
| WO | WO 2008/090093 | 7/2008 | | |

OTHER PUBLICATIONS

Schulte et al (2006, Accession No. BX842595).*
Schulte et al (2005, Accession No. Q6MWQ3_NEUCR).*
Galagan et al, 2005, Nature, 438:1105-1115.*
IBIS Access No. ADU07756, Jan. 13, 2005.
IBIS Access No. ASP18020, Oct. 16, 2008.
UniProt Access No. Q7SCE9, Dec. 15, 2003.
UniProt Q6MWQ3, Jul. 5, 2004.
Borkovich et al., Lessons from the Genome Sequence of Neurospora crassa: Tracing the Path from Genomic Blueprint to Multicellular Organism, 2004, Microbiol Mol Biol Revs, 68 (1), pp. 1-108.
Q5B1W7 [UniParc]—putative uncharacterized protein—Emericella nidulans (Apr. 2005).
Q2U8Y3 [UniParc]—predicted protein—Aspergillus oryzae (Jan. 2006).
Galagan et al, 2003, Nature 422(6934), 859-869.
Nakamura et al, 2006, Biosci, Biotechnol Biochem 70(10), 2363-2370.
WO 2004-091544—Geneseq Access No. ADU07756, 2004.

* cited by examiner

*Primary Examiner* — Jason Deveau Rosen
(74) *Attorney, Agent, or Firm* — Michael W. Krenicky

(57) ABSTRACT

The present invention relates to isolated polypeptides having amylolytic enhancing activity and isolated polynucleotides encoding the polypeptides. The invention also relates to nucleic acid constructs, vectors, and host cells comprising the polynucleotides as well as methods of producing and using the polypeptides.

8 Claims, 13 Drawing Sheets

```
ATGAAGTTCTCCATCATCTCGGTTGCCCTTGCATCGGCCATAACGGTCGACGCCCATGGATATTTGACCATTCCA   75
 M  K  F  S  I  I  S  V  A  L  A  S  A  I  T  V  D  A  H  G  Y  L  T  I  P
TTCAGTCGTACAAGACTTGGCGCAGAGGTAAACAAATACCCTGAAGATCGTTAGAAGATTGATCGTGCTGATTTG  150
 F  S  R  T  R  L  G  A  E
TGTTTTCTAGGCCGGCTTGGACACTTGTCCCGAGTGCTCCATTCTGGAGCCCGTGACGGCATGGCCCAACGTTAC  225
                A  G  L  D  T  C  P  E  C  S  I  L  E  P  V  T  A  W  P  N  V  T
GGAAGCCAAGGTCGGCAGAAGCGGTCCTTGCGGCTACAATGCCCGCGTCAGCATCGACTACAACCAGCCTGCGAC  300
  E  A  K  V  G  R  S  G  P  C  G  Y  N  A  R  V  S  I  D  Y  N  Q  P  A  T
TAACTGGGGTAACTCTCCTGTCGTGACGTACACTGCCGGCGACACTGTCGATGTCCAGTGGTGCGTTGACCACAA  375
  N  W  G  N  S  P  V  V  T  Y  T  A  G  D  T  V  D  V  Q  W  C  V  D  H  N
CGGCGACCACGGTGGCATGTTCTCCTACCGTATCTGCCAAGACCAAGAGCTGGTCAACAAATTCCTCACTCCTGG  450
  G  D  H  G  G  M  F  S  Y  R  I  C  Q  D  Q  E  L  V  N  K  F  L  T  P  G
ATATCTCCCGACCGAGGCGGAGAAGCAGGCTGCTGAGGATTGCTTCGAGAAGGGCACCCTTCCCTGCACAGATGT  525
  Y  L  P  T  E  A  E  K  Q  A  A  E  D  C  F  E  K  G  T  L  P  C  T  D  V
GAATGGCCAATCTTGCGACTTCAGCCCTGACTGCCAGCAAGGCCAGGCATGCTGGAGGAACGACTGGTTCAGTAA  600
  N  G  Q  S  C  D  F  S  P  D  C  Q  Q  G  Q  A  C  W  R  N  D  W  F
GTTAGCCTGCATCAGTAGGAAGAAGCATCCTGCTAATCGTCGTGTGACTTACTTAGCCTGCAACGCCTTTCAAGC  675
                                                           T  C  N  A  F  Q  A
TGACAGCCGCCGTGGCTGCCAGGGCGTCGACAACGCTGCTCTCGGATCTTGCTTCACCACCATCGCTGGCGGCTA  750
  D  S  R  R  G  C  Q  G  V  D  N  A  A  L  G  S  C  F  T  T  I  A  G  G  Y
CACCGTCACCAAGAAGATCAAGATACCCAACTACATCTCCGGCCACACCTTGCTCTCCTTCCGGTGGAACTCCTT  825
  T  V  T  K  K  I  K  I  P  N  Y  I  S  G  H  T  L  L  S  F  R  W  N  S  F
CCAAACTGCTCAGGTCTACCTCTCGTGCGCCGACATCGCCATTGTCGGCGACAGCGCCTCCACCACCAAAGTCTC  900
  Q  T  A  Q  V  Y  L  S  C  A  D  I  A  I  V  G  D  S  A  S  T  T  K  V  S
TGCCACCGCCACGACTCTTGTCACCAGCAGCAAGACTGCCAGCGCCTCTTGCACCCCCGCCGCCACCGTGCTGT  975
  A  T  A  T  T  L  V  T  S  S  K  T  A  S  A  S  C  T  P  A  A  T  V  A  V
GACTTTCAACCACCTCGCCAGCACCAGCTACGGCGAGTCCATCAAGATCGTTGGTTCGATCTCGCAGCTCGGCAG 1050
  T  F  N  H  L  A  S  T  S  Y  G  E  S  I  K  I  V  G  S  I  S  Q  L  G  S
CTGGAGCGCCTCGTCCGGCGTTGCCTTGTCTGCGTCGCAGTACACCACCAGCAACCCGTTTGGACTGCCACGGT 1125
  W  S  A  S  S  G  V  A  L  S  A  S  Q  Y  T  T  S  N  P  L  W  T  A  T  V
CAGTCTCCCGGCGGGCACCAAGTTCGAGTACAAGTTCGTCAAGGTGTCTAGCGAAGGCAGTGCCGTGACATGGGA 1200
  S  L  P  A  G  T  K  F  E  Y  K  F  V  K  V  S  S  E  G  S  A  V  T  W  E
GAGCGATCCCAATAGGTCGTATACTGTTCCTCAGAGCTGCGCTGAGTCGGTAGCTGTTGAGTCGTCGTGGAAGTA 1275
  S  D  P  N  R  S  Y  T  V  P  Q  S  C  A  E  S  V  A  V  E  S  S  W  K  .
G 1276
```

Fig. 2

```
ATGAAGTCTCTCCTCGCCCTTGTGGCAGGAAATCTCGTCACTGCTGTGTCTGGTCATGGGTATTTGACTGTCCCC    75
 M  K  S  L  L  A  L  V  A  G  N  L  V  T  A  V  S  G  H  G  Y  L  T  V  P
GCAAGCCGTACCCGTCTGGGCTTCGAG GTAAGCAAATCTCAGTCTGTTTCAGTATGCACCAGGTTCTAATGCGTG   150
 A  S  R  T  R  L  G  F  E
CGTGAGTATAGGCTGGAATAGATACGTGCCCGGAATGCTCGATCCTCGAGCCGGTATCTGCATGGCCAGATCTGA   225
               A  G  I  D  T  C  P  E  C  S  I  L  E  P  V  S  A  W  P  D  L
CTGCCGGCCCAGGTTGGTAGAAGTGGTCCCTGCGGTTACAACGCTCGGGTGAGTGTGGATTACAATCAGCCTGGAG   300
 T  A  A  Q  V  G  R  S  G  P  C  G  Y  N  A  R  V  S  V  D  Y  N  Q  P  G
ATTACTGGGGAAACGAGCCGGTGGTCTCCTATACTGCTGGTGATGTCGTTGAAGTACAGTGGTGTGTAGACCACA   375
 D  Y  W  G  N  E  P  V  V  S  Y  T  A  G  D  V  V  E  V  Q  W  C  V  D  H
ATGGGGATCATGGTGGAATGTTTACATATGGTATCTGCCAGAACCAAACCTTGGTGGACCTGTTCTTGACCCCTG   450
 N  G  D  H  G  G  M  F  T  Y  G  I  C  Q  N  Q  T  L  V  D  L  F  L  T  P
GCTATCTGCCAACAAACGAAGAGAAGCAAGCTGCAGAAGACTGCTTCTTAGAAGGTGAACTCAGTTGCCTTCATG   525
 G  Y  L  P  T  N  E  E  K  Q  A  A  E  D  C  F  L  E  G  E  L  S  C  L  H
TCCCCGGACAGACCTGCAATTACAACCCCGATTGCAGTGCAGGTGAGCCATGTTATCAAAACGACTGGTTCACCT   600
 V  P  G  Q  T  C  N  Y  N  P  D  C  S  A  G  E  P  C  Y  Q  N  D  W  F  T
GCAATGCTTTCCAGGCAGACAACAATCGCGCATGCCAAGGGGTCGACGGGGCAGCGTTGAACTCCTGCATGACCA   675
 C  N  A  F  Q  A  D  N  N  R  A  C  Q  G  V  D  G  A  A  L  N  S  C  M  T
CGATCGCCGGTGGATACACCGTGACCAAGAAGATCAAGATCCCCGATTACTCATCCAGCCATACCCTCCTCCGAT   750
 T  I  A  G  G  Y  T  V  T  K  K  I  K  I  P  D  Y  S  S  S  H  T  L  L  R
TCAGATGGAATTCGTTCCAGACAGCCCAGGTGTATCTGCACTGCGCTGATATTGCTATTGTGGGTGGTAGTGGTT   825
 F  R  W  N  S  F  Q  T  A  Q  V  Y  L  H  C  A  D  I  A  I  V  G  G  S  G
CATCACCTAGCCCTACTTCGACCACATCCACTGCTACCTCAACGACTACACCTTCTTCCACCAGCTGCGCGTCCG   900
 S  S  P  S  P  T  S  T  T  S  T  A  T  S  T  T  T  P  S  S  T  S  C  A  S
CAATCTCTATACCGGTGACGTTCAACGCGCTTGTTACAACTACCTATGGTGAGAACGTGTACCTTGCCGGATCCA   975
 A  I  S  I  P  V  T  F  N  A  L  V  T  T  T  Y  G  E  N  V  Y  L  A  G  S
TCAGCCAGCTAGGTTCCTGGTCGACTAGCTCTGCCGTTGCTCTATCTGCCAGCAAATATAGTTCGTCCAGCCCAC   1050
 I  S  Q  L  G  S  W  S  T  S  S  A  V  A  L  S  A  S  K  Y  S  S  S  P
TATGGACCGTGACAGTCGACCTCCCAGTCGGGGCCACATTCGAATACAAGTATATCAAGAAGGAGTCGGATGGAA   1125
 L  W  T  V  T  V  D  L  P  V  G  A  T  F  E  Y  K  Y  I  K  K  E  S  D  G
GTATTGTCTGGGAGAGTGGCCCGAACAGGAGCTACACTGTGCCGACTGGCTGTTCGGGGACAACCGCCACAGAGA   1200
 S  I  V  W  E  S  G  P  N  R  S  Y  T  V  P  T  G  C  S  G  T  T  A  T  E
GTGGTGCATGGCGGTAG    1217
 S  G  A  W  R  .
```

Fig. 4

```
ATGAAGGTCTTCGCCCCATTACTCTCCCTCAGTTTAGCTACCTCCGTAGCAGGCCATGGCTACATGTACATCCCT    75
 M   K   V   F   A   P   L   L   S   L   S   L   A   T   S   V   A   G   H   G   Y   M   Y   I   P
TCTAGCCGAACCCGTCTTGGTCACGAGGCCGGTATCGACTCATGCCCTGAGTGTGCGATCCTCGAGCCCGTTTCC   150
 S   S   R   T   R   L   G   H   E   A   G   I   D   S   C   P   E   C   A   I   L   E   P   V   S
TCCTGGCCAGACCTCGATGCGGCACCAGTTGGCCGCAGTGGACCCTGCGGTTACAACGCCCGTGACAGTATCGAC   225
 S   W   P   D   L   D   A   A   P   V   G   R   S   G   P   C   G   Y   N   A   R   D   S   I   D
TACAACCAGCCAACCACCAACTGGGGCTCCGACGCTGTGCAAAGCTACAGCCCCGGCGAAGAGATCGAAGTACAG   300
 Y   N   Q   P   T   T   N   W   G   S   D   A   V   Q   S   Y   S   P   G   E   E   I   E   V   Q
TGGTGTGTTGACCACAACGGTGACCATGGTGGCATGTTCACGTACCGGATCTGTCAAGACCAGAGCATTGTCGAC   375
 W   C   V   D   H   N   G   D   H   G   G   M   F   T   Y   R   I   C   Q   D   Q   S   I   V   D
AAGTTTCTCGACCCGTCTTACCTGCCCACCAACGACGAGAAGCAGGCTGCTGAGGATTGTTTCGACGCAGGTCTG   450
 K   F   L   D   P   S   Y   L   P   T   N   D   E   K   Q   A   A   E   D   C   F   D   A   G   L
CTACCCTGCACGGATGTCAGTGGCCAGGAGTGTGGGTACAGTGCGGATTGTACCGAGGGCGAGGCCTGCTGGCGT   525
 L   P   C   T   D   V   S   G   Q   E   C   G   Y   S   A   D   C   T   E   G   E   A   C   W   R
AATGATTGGTTTACGTGCAATGGCTTCGAGGCTTCTGACCGGCCTAAGTGCCAGGGTGTTGACAATGCAGAGTTG   600
 N   D   W   F   T   C   N   G   F   E   A   S   D   R   P   K   C   Q   G   V   D   N   A   E   L
AACTCCTGCTATACCAGTATTGCTGGTGGATACACGGTGACCAAGAAGGTCAAGCTGCCGGAGTACACTTCCAAC   675
 N   S   C   Y   T   S   I   A   G   G   Y   T   V   T   K   K   V   K   L   P   E   Y   T   S   N
CATACCTTGATTTCGTTCAAGTGGAACTCGTTCCAGACTGGCCAGATTTACCTGTCTTGTGCTGATATTGCCATT   750
 H   T   L   I   S   F   K   W   N   S   F   Q   T   G   Q   I   Y   L   S   C   A   D   I   A   I
CAGTGA   756
 Q   .
```

POLYPEPTIDES HAVING AMYLOLYTIC ENHANCING ACTIVITY AND POLYNUCLEOTIDES ENCODING SAME

CROSS-REFERENCE TO RELATED APPLICATIONS

This application is a 35 U.S.C. 371 national application of PCT/US2009/062955 filed on Nov. 2, 2009 and claims priority from U.S. provisional application Ser. No. 61/120, 617 filed Dec. 8, 2008 and U.S. provisional application Ser. No. 61/116,605 filed Nov. 20, 2008, which applications are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having amylolytic enhancing activity and isolated polynucleotides encoding the polypeptides. The invention also relates to nucleic acid constructs, vectors, and host cells comprising the polynucleotides as well as methods of producing and using the polypeptides.

2. Description of the Related Art

Starch is a complex carbohydrate composed of two main components: amylopectin and amylose. Amylose is a straight chain molecule while amylopectin is a branched molecule. Amylose is composed of D-glucose molecules that are linked by alpha-1,4-glycosidic bonds. Amyopectin is composed of D-glucose molecules that are linked by alpha-1,4-glycosidic bonds as well as D-glucose molecules linked by alpha-1,6-glycosidic bonds. The alpha-1,6-glycosidic linkages give rise to branching. The ratio of amylose to amylopectin varies among sources of starch.

Starch can be hydrolyzed into simpler carbohydrates by acids, various enzymes, or a combination thereof. The extent of conversion is typically quantified by dextrose equivalency (DE), which relates to the fraction of the glycoside bonds in starch that have been cleaved. The primary enzymes used to hydrolyze starch into simpler carbohydrates are endoamylases, exoamylases, and debranching enzymes, which hydrolyze amylose and amylopectin. Amylose is hydrolyzed mainly by amylases, while amylopectin also requires debranching enzymes such as pullulanases (E.C. 3.2.1.41) for complete hydrolysis. The endoamylases, the most common being alpha-amylase (E.C. 3.2.1.1), are specific for alpha-1,4-linkages of amylose and amylopectin. Exoamylases have the ability to hydrolyze both alpha-1,4-linkages and alpha-1,6-linkages of amylose and amylopectin. A common example is amyloglucosidase (E.C. 3.2.1.20). Beta-amylase is an enzyme that has the ability to hydrolyze the alpha-1, 4-linkages of amylose. Debranching enzymes, e.g., pullulanases, hydrolyze alpha-1,6-linkages in amylopectin. Hydrolysis products of debranching enzymes are mainly maltotriose and maltose.

There are many food products that are produced from starch, which include, for example, maltodextrin, a lightly hydrolyzed (DE 10-20) starch product used as a bland-tasting filler and thickener; various corn syrups (DE 30-70), viscous solutions used as sweeteners and thickeners in many kinds of processed foods; dextrose (DE 100), commercial glucose, prepared by the complete hydrolysis of starch; and high fructose syrup, made by treating dextrose solutions with the enzyme glucose (xylose) isomerase, until a substantial fraction of the glucose has been converted to fructose.

It would be advantageous in the art to improve the enzymatic conversion of starch-containing materials.

The present invention provides isolated polypeptides having amylolytic enhancing activity and polynucleotides encoding the polypeptides and processes for their use.

SUMMARY OF THE INVENTION

The present invention relates to isolated polypeptides having amylolytic enhancing activity selected from the group consisting of:

(a) a polypeptide comprising an amino acid sequence having at least 60% sequence identity to the mature polypeptide of SEQ ID NO: 2, SEQ ID NO: 4, or SEQ ID NO: 6;

(b) a polypeptide encoded by a polynucleotide that hybridizes under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii);

(c) a polypeptide encoded by a polynucleotide comprising a nucleotide sequence having at least 60% sequence identity to the mature polypeptide coding sequence of SEQ ID NO: 1, SEQ ID NO: 3, or SEQ ID NO: 5;

(d) a polypeptide comprising one or more of the motifs selected from the group consisting of N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20); and (e) a variant comprising a substitution, deletion, and/or insertion of one or more (several) amino acids of the mature polypeptide of SEQ ID NO: 2, SEQ ID NO: 4, or SEQ ID NO: 6.

The present invention also relates to isolated polynucleotides encoding polypeptides having amylolytic enhancing activity, selected from the group consisting of:

(a) a polynucleotide encoding a polypeptide comprising an amino acid sequence having at least 60% sequence identity to the mature polypeptide of SEQ ID NO: 2, SEQ ID NO: 4, or SEQ ID NO: 6;

(b) a polynucleotide that hybridizes under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii);

(c) a polynucleotide comprising a nucleotide sequence having at least 60% sequence identity to the mature polypeptide coding sequence of SEQ ID NO: 1, SEQ ID NO: 3, or SEQ ID NO: 5;

(d) a polynucleotide encoding a polypeptide comprising one or more of the motifs selected from the group consisting of N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20); and (e) a polynucleotide encoding a variant comprising a substitution, deletion, and/or insertion of one or more (several) amino acids of the mature polypeptide of SEQ ID NO: 2, SEQ ID NO: 4, or SEQ ID NO: 6.

The present invention also relates to nucleic acid constructs, recombinant expression vectors, and recombinant host cells comprising the polynucleotides, and to methods of producing the polypeptides having amylolytic enhancing activity.

The present invention also relates to methods of inhibiting the expression of a polypeptide having amylolytic enhancing activity in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to processes for the polypeptides having amylolytic enhancing activity in the degradation of starch.

The present invention also relates to plants comprising an isolated polynucleotide encoding a polypeptide having amylolytic enhancing activity.

The present invention also relates to methods of producing a polypeptide having amylolytic enhancing activity, comprising: (a) cultivating a transgenic plant or a plant cell comprising a polynucleotide encoding the polypeptide having amylolytic enhancing activity under conditions conducive for production of the polypeptide; and (b) recovering the polypeptide.

The present invention also relates to an isolated polynucleotide encoding a signal peptide comprising or consisting of amino acids 1 to 18 of SEQ ID NO: 2, amino acids 1 to 18 of SEQ ID NO: 4, or amino acids 1 to 18 of SEQ ID NO: 6; to nucleic acid constructs, expression vectors, and recombinant host cells comprising the polynucleotides; and to methods of producing a protein.

BRIEF DESCRIPTION OF THE FIGURES

FIG. 2 shows the genomic DNA sequence and the deduced amino acid sequence of a *Neurospora crassa* FGSC 2489 polypeptide having amylolytic enhancing activity (SEQ ID NOs: 1 and 2, respectively).

FIG. 4 shows the genomic DNA sequence and the deduced amino acid sequence of an *Aspergillus nidulans* FGSC A1000 polypeptide having amylolytic enhancing activity (SEQ ID NOs: 3 and 4, respectively).

FIG. 12 shows the cDNA sequence and the deduced amino acid sequence of an *Aspergillus oryzae* IFO 4177 polypeptide having amylolytic enhancing activity (SEQ ID NOs: 5 and 6, respectively).

DEFINITIONS

Figure 1:
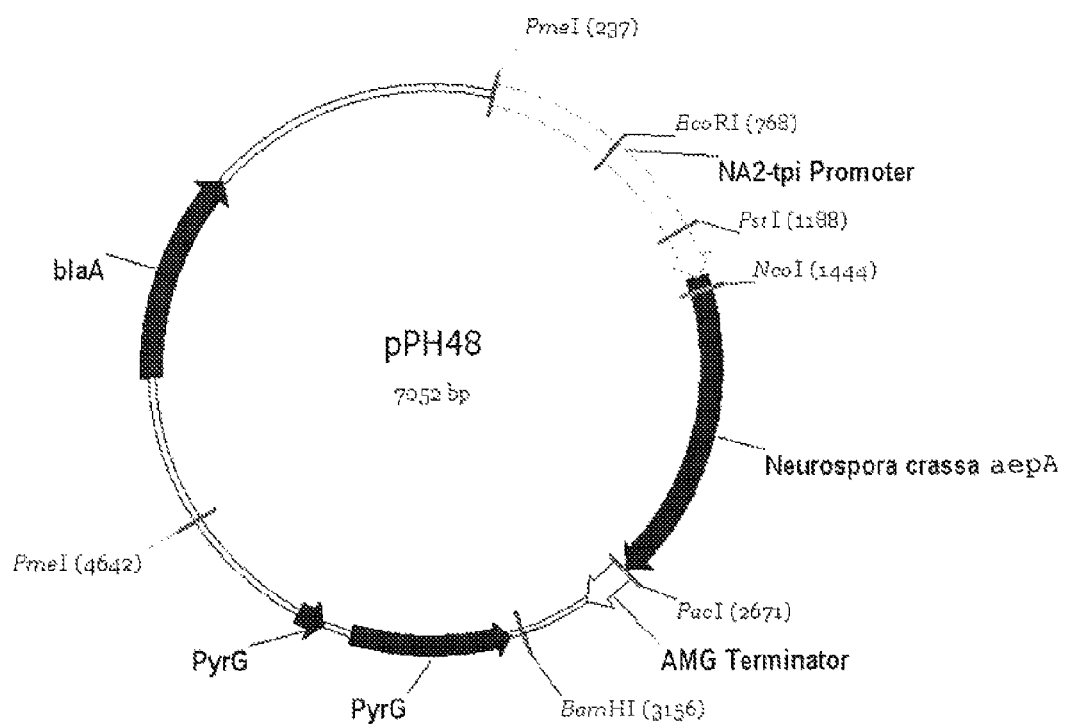
FIG. 1 shows a restriction map of pPH48.

Amylolytic enhancing activity: The term "amylolytic enhancing activity" is defined herein as a biological activity that enhances the hydrolysis of a starch by proteins having amylolytic activity. For purposes of the present invention, amylolytic enhancing activity is determined by measuring the increase in reducing sugars from the hydrolysis of a starch by an amylolytic enzyme under conditions of pH and temperature that are preferably optimal for the amylolytic enzyme.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the amylolytic enhancing activity of the mature polypeptide of SEQ ID NO: 2, SEQ ID NO: 4, or SEQ ID NO: 6.

The polypeptides having amylolytic enhancing activity enhance the hydrolysis of a starch-containing material catalyzed by proteins having amylolytic activity by reducing the amount of amylolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Starch-containing material: The term "starch-containing material" is defined herein as a any material comprising starch, which is a polysaccharide carbohydrate $(C_6H_{10}O_5)_n$ consisting of a large number of glucose monosaccharide units joined together by alpha-1,4-glycosidic bonds or alpha-1,4-glycosidic bonds and alpha-1,6-glycosidic bonds. Starch is especially found in seeds, bulbs, and tubers. In the methods of the present invention, the starch-containing material can be any material containing starch. Starch is generally obtained from the seeds of plants, such as corn, wheat, sorghum, or rice; and from the tubers and roots of plants such as cassava, potato, arrowroot, tapioca, and the pith of sago palm. Examples of starch-containing starting materials suitable for use in a process of the present invention include, but are not limited to, tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley. The major commercial source of starch is corn, from which starch is extracted by wet milling processes. The starch-containing material can also be lignocellulose containing starch.

In one aspect, the starch-containing material is corn starch. In another aspect, the starch-containing material is wheat starch. In another aspect, the starch-containing material is sorghum starch. In another aspect, the starch-containing material is rice starch. In another aspect, the starch-containing material is cassava starch. In another aspect, the starch-containing material is potato starch. In another aspect, the starch-containing material is arrowroot starch. In another aspect, the starch-containing material is tapioca starch. In another aspect, the starch-containing material is sago palm starch.

The term "granular starch" means raw uncooked starch, i.e., starch in its natural form found in cereal, tubers or grains. Starch is formed within plant cells as tiny granules insoluble in water. When placed in cold water, the starch granules can absorb a small amount of the liquid and swell. At temperatures up to 50° C. to 75° C. the swelling can be reversible. However, with higher temperatures an irreversible swelling called "gelatinization" begins. Granular starch can be a highly refined starch, preferably at least 90%, more preferably at least 95%, more preferably at least 97%, and most preferably at least 99.5% pure, or it may be a more crude starch containing material comprising milled whole grain including non-starch fractions such as germ residues and fibers. The raw material, such as whole grain, is milled in order to open up the structure for further processing. Two milling processes are preferred: wet and dry milling. In dry milling whole kernels are milled and used. Wet milling gives a good separation of germ and meal (starch granules and protein) and is often applied at locations where starch hydrolysate is used in production of syrups. Both dry and wet milling are well known in the art of starch processing.

The starch-containing material may be reduced in particle size, preferably by dry or wet milling, in order to expose more surface area. In one aspect, the particle size is preferably between 0.05 to 3.0 mm, more preferably between 0.1 to 1.5 mm, and most preferably between 0.1 to 0.5 mm, so that preferably at least 30%, more preferably at least 50%, even more preferably at least 70%, and most preferably at least 90% of the starch-containing material passes through a sieve with preferably a 0.05 to 3.0 mm screen, more preferably a 05 to 1.5 mm screen, and most preferably a 0.1 to 0.5 mm screen.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide in its final form following translation and any post-translational modifications, such as N-terminal processing, C-terminal truncation, glycosylation, phosphorylation, etc. In one aspect, the mature polypeptide is amino acids 19 to 385 of SEQ ID NO: 2 based on the SignalP program (Nielsen et al., 1997, Protein Engineering 10:1-6) that predicts amino acids 1 to 18 of SEQ ID NO: 2 is a signal peptide. In another aspect, the mature polypeptide is amino acids 19 to 385 of SEQ ID NO: 4 based on the SignalP program (Nielsen et al., 1997, supra) that predicts amino acids 1 to 18 of SEQ ID NO: 4 is a signal peptide. In another aspect, the mature polypeptide is amino acids 19 to 251 of SEQ ID NO: 6 based on the SignalP program (Nielsen et al., 1997, supra) that predicts amino acids 1 to 18 of SEQ ID NO: 6 is a signal peptide.

Mature polypeptide coding sequence: The term "mature polypeptide coding sequence" is defined herein as a nucleotide sequence that encodes a mature polypeptide having amylolytic enhancing activity. In one aspect, the mature polypeptide coding sequence is nucleotides 55 to 1273 of SEQ ID NO: 1 based on the SignalP program (Nielsen et al., 1997, supra) that predicts nucleotides 1 to 54 of SEQ ID NO: 1 encode a signal peptide. In another aspect, the mature polypeptide coding sequence is nucleotides 55 to 1214 of SEQ ID NO: 3 based on the SignalP program (Nielsen et al., 1997, supra) that predicts nucleotides 1 to 54 of SEQ ID NO: 3 encode a signal peptide. In another aspect, the mature polypeptide coding sequence is nucleotides 55 to 753 of SEQ ID NO: 5 based on the SignalP program (Nielsen et al., 1997, supra) that predicts nucleotides 1 to 54 of SEQ ID NO: 5 encode a signal peptide.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Homologous sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Neurospora crassa* polypeptide having amylolytic enhancing activity of SEQ ID NO: 2 or the mature polypeptide thereof, the *Aspergillus nidulans* polypeptide having amylolytic enhancing activity of SEQ ID NO: 4 or the mature polypeptide thereof, or the *Aspergillus oryzae* polypeptide having amylolytic enhancing activity of SEQ ID NO: 6 or the mature polypeptide thereof.

Polypeptide fragment: The term "polypeptide fragment" is defined herein as a polypeptide having one or more (several) amino acids deleted from the amino and/or carboxyl terminus of the mature polypeptide of SEQ ID NO: 2, SEQ ID NO: 4, or SEQ ID NO: 6; or a homologous sequence thereof; wherein the fragment has amylolytic enhancing activity. In one aspect, a fragment contains at least 312 amino acid residues, more preferably at least 330 amino acid residues, and most preferably at least 348 amino acid residues of the mature polypeptide of SEQ ID NO: 2 or a homologous sequence thereof. In another aspect, a fragment contains at least 312 amino acid residues, more preferably at least 330 amino acid residues, and most preferably at least 348 amino acid residues of the mature polypeptide of SEQ ID NO: 4 or a homologous sequence thereof. In another aspect, a fragment contains at least 200 amino acid residues, more preferably at least 210 amino acid residues, and most preferably at least 220 amino acid residues of the mature polypeptide of SEQ ID NO: 6 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1, SEQ ID NO: 3, or SEQ ID NO: 5; or a homologous sequence thereof; wherein the subsequence encodes a polypeptide fragment having amylolytic enhancing activity. In one aspect, a subsequence contains at least 936 nucleotides, more preferably at least 990 nucleotides, and most preferably at least 1044 nucleotides of the mature polypeptide coding sequence of SEQ ID NO: 1 or a homologous sequence thereof. In another aspect, a subsequence contains at least 936 nucleotides, more preferably at least 990 nucleotides, and most preferably at least 1044 nucleotides of the mature polypeptide coding sequence of SEQ ID NO: 3 or a homologous sequence thereof. In another aspect, a subsequence contains at least 600 nucleotides, more preferably at least 6300 nucleotides, and most preferably at least 660 nucleotides of the mature polypeptide coding sequence of SEQ ID NO: 5 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide comprising or consisting of the mature polypeptide of SEQ ID NO: 2, SEQ ID NO: 4, or SEQ ID NO: 6; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having amylolytic enhancing activity produced by an organism expressing a modified polynucleotide sequence of the mature polypeptide coding sequence of SEQ ID NO: 1, SEQ ID NO: 3, or SEQ ID NO: 5; or a homologous sequence thereof. The modified nucleotide sequence is obtained through human intervention by modification of the polynucleotide sequence disclosed in SEQ ID NO: 1, SEQ ID NO: 3, or SEQ ID NO: 5; or a homologous sequence thereof.

DETAILED DESCRIPTION OF THE INVENTION

Polypeptides Having Amylolytic Enhancing Activity

In a first aspect, the present invention relates to isolated polypeptides comprising amino acid sequences having a degree of sequence identity to the mature polypeptide of SEQ ID NO: 2, SEQ ID NO: 4, or SEQ ID NO: 6 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have amylolytic enhancing activity (hereinafter "homologous polypeptides"). In a preferred aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 2, SEQ ID NO: 4, or SEQ ID NO: 6.

A polypeptide of the present invention preferably comprises the amino acid sequence of SEQ ID NO: 2 or an allelic variant thereof; or a fragment thereof having amylolytic enhancing activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 19 to 385 of SEQ ID NO: 2, or an allelic variant thereof; or a fragment thereof having amylolytic enhancing activity. In another preferred aspect, the polypeptide comprises amino acids 19 to 385 of SEQ ID NO: 2. In another preferred aspect, the polypeptide consists of the amino acid sequence of SEQ ID NO: 2 or an allelic variant thereof; or a fragment thereof having amylolytic enhancing activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 19 to 385 of SEQ ID NO: 2 or an allelic variant thereof; or a fragment thereof having amylolytic enhancing activity. In another preferred aspect, the polypeptide consists of amino acids 19 to 385 of SEQ ID NO: 2.

A polypeptide of the present invention preferably comprises the amino acid sequence of SEQ ID NO: 4 or an allelic variant thereof; or a fragment thereof having amylolytic enhancing activity. In a preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 19 to 385 of SEQ ID NO: 4, or an allelic variant thereof; or a fragment thereof having amylolytic enhancing activity. In another preferred aspect, the polypeptide comprises amino acids 19 to 385 of SEQ ID NO: 4. In another preferred aspect, the polypeptide consists of the amino acid sequence of SEQ ID NO: 4 or an allelic variant thereof; or a fragment thereof having amylolytic enhancing activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 19 to 385 of SEQ ID NO: 4 or an allelic variant thereof; or a fragment thereof having amylolytic enhancing activity. In another preferred aspect, the polypeptide consists of amino acids 19 to 385 of SEQ ID NO: 4.

A polypeptide of the present invention preferably comprises the amino acid sequence of SEQ ID NO: 6 or an allelic variant thereof; or a fragment thereof having amylolytic enhancing activity. In a preferred aspect, the polypeptide comprises the amino acid sequence of SEQ ID NO: 6. In another preferred aspect, the polypeptide comprises the mature polypeptide of SEQ ID NO: 6. In another preferred aspect, the polypeptide comprises amino acids 19 to 251 of SEQ ID NO: 6, or an allelic variant thereof; or a fragment thereof having amylolytic enhancing activity. In another preferred aspect, the polypeptide comprises amino acids 19 to 251 of SEQ ID NO: 6. In another preferred aspect, the polypeptide consists of the amino acid sequence of SEQ ID NO: 6 or an allelic variant thereof; or a fragment thereof having amylolytic enhancing activity. In another preferred aspect, the polypeptide consists of the amino acid sequence of SEQ ID NO: 6. In another preferred aspect, the polypeptide consists of the mature polypeptide of SEQ ID NO: 6. In another preferred aspect, the polypeptide consists of amino acids 19 to 251 of SEQ ID NO: 6 or an allelic variant thereof; or a fragment thereof having amylolytic enhancing activity. In another preferred aspect, the polypeptide consists of amino acids 19 to 251 of SEQ ID NO: 6.

In a second aspect, the present invention relates to isolated polypeptides having amylolytic enhancing activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The nucleotide sequence of SEQ ID NO: 1, SEQ ID NO: 3, or SEQ ID NO: 5; or a subsequence thereof; as well as the amino acid sequence of SEQ ID NO: 2, SEQ ID NO: 4, or SEQ ID NO: 6; or a fragment thereof; may be used to design nucleic acid probes to identify and clone DNA encoding polypeptides having amylolytic enhancing activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having amylolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, or SEQ ID NO: 5, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, or SEQ ID NO: 5; the cDNA sequence contained in the mature polypeptide coding sequence of SEQ ID NO: 1 or SEQ ID NO: 3 or the genomic DNA sequence comprising the mature polypeptide coding sequence of SEQ ID NO: 5; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 55 to 1273 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1.

In another preferred aspect, the nucleic acid probe is the mature polypeptide coding sequence of SEQ ID NO: 3. In another preferred aspect, the nucleic acid probe is nucleotides 55 to 1214 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3.

In another preferred aspect, the nucleic acid probe is the mature polypeptide coding sequence of SEQ ID NO: 5. In another preferred aspect, the nucleic acid probe is nucleotides 55 to 753 of SEQ ID NO: 5. In another preferred aspect, the nucleic acid probe is a polynucleotide sequence that encodes the polypeptide of SEQ ID NO: 6, or a subsequence thereof. In another preferred aspect, the nucleic acid probe is SEQ ID NO: 5.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having amylolytic enhancing activity encoded by polynucleotides comprising or consisting of nucleotide sequences having a degree of sequence identity to the mature polypeptide coding sequence of SEQ ID NO: 1, SEQ ID NO: 3, or SEQ ID NO: 5 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having amylolytic enhancing activity. See polynucleotide section herein.

In a fourth aspect, the present invention relates to isolated polypeptides having amylolytic enhancing activity, comprising one or more of the motifs selected from the group consisting of N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20). In these motifs, the accepted IUPAC single letter amino acid abbreviation is employed.

In a preferred aspect, the isolated polypeptide having amylolytic enhancing activity comprises N-G-D-H-G-G-M (SEQ ID NO: 17). In another preferred aspect, the isolated polypeptide having amylolytic enhancing activity comprises Q-T-x-Q-x-Y-L-x-C-A-D (SEQ ID NO: 18). In another preferred aspect, the isolated polypeptide having amylolytic enhancing activity comprises E-K-x-A-A-E-x-C-F (SEQ ID NO: 19). In another preferred aspect, the isolated polypeptide having amylolytic enhancing activity comprises Y-N-A-R-x(3)-D-Y-N-[FQVP] (SEQ ID NO: 20).

In another preferred aspect, the isolated polypeptide having amylolytic enhancing activity comprises N-G-D-H-G-G-M (SEQ ID NO: 17) and Q-T-x-Q-x-Y-L-x-C-A-D (SEQ ID NO: 18). In another preferred aspect, the isolated polypeptide having amylolytic enhancing activity comprises N-G-D-H-G-G-M (SEQ ID NO: 17) and E-K-x-A-A-E-x-C-F (SEQ ID NO: 19). In another preferred aspect, the isolated polypeptide having amylolytic enhancing activity comprises N-G-D-H-G-G-M (SEQ ID NO: 17) and Y-N-A-R-x(3)-D-Y-N-[FQVP] (SEQ ID NO: 20). In another preferred aspect, the isolated polypeptide having amylolytic enhancing activity comprises Q-T-x-Q-x-Y-L-x-C-A-D (SEQ ID NO: 18) and E-K-x-A-A-E-x-C-F (SEQ ID NO: 19). In another preferred aspect, the isolated polypeptide having amylolytic enhancing activity comprises Q-T-x-Q-x-Y-L-x-C-A-D (SEQ ID NO: 18) and Y-N-A-R-x(3)-D-Y-N-[FQVP] (SEQ ID NO: 20). In another preferred aspect, the isolated polypeptide having amylolytic enhancing activity comprises E-K-x-A-A-E-x-C-F (SEQ ID NO: 19) and Y-N-A-R-x(3)-D-Y-N-[FQVP] (SEQ ID NO: 20).

In another preferred aspect, the isolated polypeptide having amylolytic enhancing activity comprises N-G-D-H-G-G-M (SEQ ID NO: 17), Q-T-x-Q-x-Y-L-x-C-A-D (SEQ ID NO: 18), and E-K-x-A-A-E-x-C-F (SEQ ID NO: 19). In another preferred aspect, the isolated polypeptide having amylolytic enhancing activity comprises N-G-D-H-G-G-M (SEQ ID NO: 17), E-K-x-A-A-E-x-C-F, and Y-N-A-R-x(3)-D-Y-N-[FQVP] (SEQ ID NO: 20). In another preferred aspect, the isolated polypeptide having amylolytic enhancing activity comprises Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20). In another preferred aspect, the isolated polypeptide having amylolytic enhancing activity comprises N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20).

In another preferred aspect, the isolated polypeptide having amylolytic enhancing activity comprises N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20).

In a fifth aspect, the present invention relates to artificial variants comprising a substitution, deletion, and/or insertion of one or more (or several) amino acids of the mature polypeptide of SEQ ID NO: 2, SEQ ID NO: 4, or SEQ ID NO: 6, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., amylolytic enhancing activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, SEQ ID NO: 4, or SEQ ID NO: 6 is 10, preferably 9, more preferably 8, more preferably 7, more preferably at most 6, more preferably 5, more preferably 4, even more preferably 3, most preferably 2, and even most preferably 1.

Sources of Polypeptides Having Amylolytic Enhancing Activity

A polypeptide having amylolytic enhancing activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having amylolytic enhancing activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having amylolytic enhancing activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having amylolytic enhancing activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having amylolytic enhancing activity.

In another preferred aspect, the polypeptide is a *Streptococcus equisimilis, Streptococcus pyogenes, Streptococcus uberis,* or *Streptococcus equi* subsp. *Zooepidemicus* polypeptide having amylolytic enhancing activity.

In another preferred aspect, the polypeptide is a *Streptomyces achromogenes, Streptomyces avermitilis, Streptomyces coelicolor, Streptomyces griseus,* or *Streptomyces lividans* polypeptide having amylolytic enhancing activity.

A polypeptide having amylolytic enhancing activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having amylolytic enhancing activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having amylolytic enhancing activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having amylolytic enhancing activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum,*

*Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having amylolytic enhancing activity.

In a more preferred aspect, the polypeptide is a *Neurospora crassa* polypeptide having amylolytic enhancing activity. In a most preferred aspect, the polypeptide is a *Neurospora crassa* FGSC 2489 polypeptide having amylolytic enhancing activity, e.g., the polypeptide comprising the mature polypeptide of SEQ ID NO: 2.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae* polypeptide.

In another more preferred aspect, the polypeptide is an *Aspergillus nidulans* polypeptide having amylolytic enhancing activity. In a most preferred aspect, the polypeptide is an *Aspergillus nidulans* FGSC A1000 polypeptide having amylolytic enhancing activity, e.g., the polypeptide comprising the mature polypeptide of SEQ ID NO: 4.

In another more preferred aspect, the polypeptide is an *Aspergillus oryza* polypeptide having amylolytic enhancing activity. In a most preferred aspect, the polypeptide is an *Aspergillus oryzae* IFO 4177 polypeptide having amylolytic enhancing activity, e.g., the polypeptide comprising the mature polypeptide of SEQ ID NO: 6.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having amylolytic enhancing activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having amylolytic enhancing activity of the present invention.

In a preferred aspect, the nucleotide sequence comprises or consists of SEQ ID NO: 1. In another preferred aspect, the nucleotide sequence comprises or consists of the mature polypeptide coding sequence of SEQ ID NO: 1. In another preferred aspect, the nucleotide sequence comprises or consists of nucleotides 55 to 1273 of SEQ ID NO: 1. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 having amylolytic enhancing activity.

In another preferred aspect, the nucleotide sequence comprises or consists of SEQ ID NO: 3. In another preferred aspect, the nucleotide sequence comprises or consists of the mature polypeptide coding sequence of SEQ ID NO: 3. In another preferred aspect, the nucleotide sequence comprises or consists of nucleotides 55 to 1214 of SEQ ID NO: 3. The present invention also encompasses nucleotide sequences that encode polypeptides comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 that encode fragments of SEQ ID NO: 4 having amylolytic enhancing activity.

In another preferred aspect, the nucleotide sequence comprises or consists of SEQ ID NO: 5. In another preferred aspect, the nucleotide sequence comprises or consists of the mature polypeptide coding sequence of SEQ ID NO: 5. In another preferred aspect, the nucleotide sequence comprises or consists of nucleotides 55 to 753 of SEQ ID NO: 5. The present invention also encompasses nucleotide sequences that encode polypeptides comprising or consisting of the amino acid sequence of SEQ ID NO: 6 or the mature polypeptide thereof, which differ from SEQ ID NO: 5 or the mature polypeptide coding sequence thereof by virtue of the degeneracy of the genetic code. The present invention also relates to subsequences of SEQ ID NO: 5 that encode fragments of SEQ ID NO: 6 having amylolytic enhancing activity.

The present invention also relates to mutant polynucleotides comprising or consisting of at least one mutation in the mature polypeptide coding sequence of SEQ ID NO: 1, SEQ ID NO: 3, or SEQ ID NO: 5, in which the mutant nucleotide sequence encodes the mature polypeptide of SEQ ID NO: 2, SEQ ID NO: 4, or SEQ ID NO: 6.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus* or *Neurospora*, or another or related organism and thus, for example, may be an allelic or species variant of the polypeptide encoding region of the nucleotide sequence.

The present invention also relates to isolated polynucleotides comprising or consisting of nucleotide sequences having a degree of sequence identity to the mature polypeptide coding sequence of SEQ ID NO: 1, SEQ ID NO: 3, or SEQ ID NO: 5 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having amylolytic enhancing activity.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, SEQ ID NO: 3, or SEQ ID NO: 5, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for amylolytic enhancing activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii); and (b) isolating the hybridizing polynucleotide, which encodes a polypeptide having amylolytic enhancing activity.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dada (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as a NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 18 of SEQ ID NO: 2. In another preferred aspect, the signal peptide coding sequence comprises or consists of nucleotides 1 to 54 of SEQ ID NO: 1.

In another preferred aspect, the signal peptide comprises or consists of amino acids 1 to 18 of SEQ ID NO: 4. In another preferred aspect, the signal peptide coding sequence comprises or consists of nucleotides 1 to 54 of SEQ ID NO: 3.

In another preferred aspect, the signal peptide comprises or consists of amino acids 1 to 18 of SEQ ID NO: 6. In another preferred aspect, the signal peptide coding sequence comprises or consists of nucleotides 1 to 54 of SEQ ID NO: 5.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention operably linked to one or more (several) control sequences that direct the production of a polypeptide having amylolytic enhancing activity. A construct or vector comprising a polynucleotide of the present invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but are not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but are not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of*

*Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Neurospora*. In a more preferred aspect, the cell is *Neurospora crassa*. In most preferred aspect, the cell is *Neurospora crassa* FGSC 2489. In another preferred aspect, the cell is of the genus *Aspergillus*. In another more preferred aspect, the cell is *Aspergillus nidulans*. In another most preferred aspect, the cell is *Aspergillus nidulans* FGSC A1000. In another more preferred aspect, the cell is *Aspergillus oryzae*. In another most preferred aspect, the cell is *Aspergillus oryzae* IFO 4177.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, SEQ ID NO: 3, or SEQ ID NO: 5, wherein the mutant nucleotide sequence encodes a polypeptide that comprises or consists of the mature polypeptide of SEQ ID NO: 2, SEQ ID NO: 4, or SEQ ID NO: 6; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having amylolytic enhancing activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having amylolytic enhancing activity of the present invention under conditions conducive for production of the polypeptide; and (b) recovering the polypeptide.

In embodiments, in addition to direct transformation of a particular plant genotype with a construct prepared according to the present invention, transgenic plants may be made by crossing a plant having a construct of the present invention to a second plant lacking the construct. For example, a construct encoding a polypeptide having amylolytic enhancing activity or a portion thereof can be introduced into a particular plant variety by crossing, without the need for ever directly transforming a plant of that given variety. Therefore, the present invention not only encompasses a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. In embodiments, crossing results in a transgene of the present invention being introduced into a plant line by cross pollinating a starting line with a donor plant line that includes a transgene of the present invention. Non-limiting examples of such steps are further articulated in U.S. Pat. No. 7,151,204.

It is envisioned that plants including a polypeptide having amylolytic enhancing activity of the present invention include plants generated through a process of backcross conversion. For examples, plants of the present invention include plants referred to as a backcross converted genotype, line, inbred, or hybrid.

In embodiments, genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

Removal or Reduction of Amylolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of amylolytic enhancing activity by fermentation of a cell that produces both a polypeptide of the present invention as well as the protein product of interest by adding an effective amount of an agent capable of inhibiting amylolytic enhancing activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of amylolytic enhancing activity by cultivating the cell under conditions permitting the expression of the product, subjecting the resultant culture broth to a combined pH and temperature treatment so as to reduce the amylolytic enhancing activity substantially, and recovering the product from the culture broth. Alternatively, the combined pH and temperature treatment may be performed on an enzyme preparation recovered from the culture broth. The combined pH and temperature treatment may optionally be used in combination with a treatment with an amylolytic enhancing inhibitor.

In accordance with this aspect of the invention, it is possible to remove at least 60%, preferably at least 75%, more preferably at least 85%, still more preferably at least 95%, and most preferably at least 99% of the amylolytic enhancing activity. Complete removal of amylolytic enhancing activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially amylolytic enhancing-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The amylolytic enhancing-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from amylolytic enhancing activity that is produced by a method of the present invention.

Methods of Inhibiting Expression of a Polypeptide Having Amylolytic Enhancing Activity The present invention also relates to methods of inhibiting the expression of a polypeptide having amylolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1, SEQ ID NO: 3, or SEQ ID NO: 5 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using the dsRNA is of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the amylolytic enhancing activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Compositions

The polypeptides of the present invention having amylolytic enhancing activity may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention. The detergent additive as well as the detergent composition may comprise one or more (several) enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757, and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/001544.

Commercially available cellulases include CELLUZYMET™ and CAREZYME™ (Novozymes A/S), CLAZINASE™ and PURADAX HA™ (Genencor International Inc.), and KAC-500(B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more (several) of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASE™, DURALASE™, ESPERASE™, and KANNASE™ (NOVOZYMES A/S); and MAXATASE™, MAXACAL™, MAXAPEM™, PROPERASE™, PURAFECTT™, PURAFECT OXP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Commercially available lipase enzymes include LIPOLASE™, LIPEX™, and LIPOLASE ULTRA™ (Novozymes A/S).

Amylases: Suitable amylases (a and/or (3) include those of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more (several) of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™, and BAN™ (Novozymes A/S); and RAPIDASE™ and PURASTAR™ (Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more (several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more (several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (several) polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention having amylolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having such hydrolytic enhancing activity may also be incorporated in the detergent formulations disclosed in WO 97/07202, which is hereby incorporated by reference.

Uses

The present invention also relates to processes for using the polypeptides having amylolytic enhancing activity, or compositions thereof. A polypeptide having amylolytic enhancing activity of the present invention in combination with other amylolytic enzymes, e.g., alpha-amylases, glucoamylases, pullulanases, etc., can be used in various applications. Such applications include, but are not limited to, starch processing; wet corn milling; alcohol production; brewing; starch desizing; detergent applications; baking applications; beverage industry; oil drilling processes; deinking of recycled paper; and animal feed.

In one aspect, the present invention relates to processes for degrading a starch-containing material, comprising: treating the starch-containing material with an enzyme composition comprising one or more (several) amylolytic enzymes in the presence of a polypeptide having amylolytic enhancing activity of the present invention. The presence of the polypeptide having amylolytic enhancing activity increases the degradation of the starch-containing material compared to the absence of the polypeptide having amylolytic enhancing activity. In a preferred aspect, the processes further comprise recovering or purifying the degraded starch-containing material. The degraded starch-containing material can be recovered or purified using any method known in the art. The degraded starch-containing material can be glucose, maltose, maltodextrin, or combinations thereof.

In another aspect, the present invention relates to processes for producing a saccharified product from a starch-containing material, comprising: (a) liquefying the starch-containing material with an alpha-amylase; and (b) saccharifying the liquefied starch-containing material with an enzyme composition comprising one or more (several) amylolytic enzymes; wherein step (a), step (b), or steps (a) and (b) are conducted in the presence of a polypeptide having amylolytic enhancing activity of the present invention. In a preferred aspect, the processes further comprise recovering or purifying the saccharified product. The saccharified product can be recovered or purified using any method known in the art. The saccharified product can be glucose, maltose, maltodextrin, or combinations thereof. In the situation where the saccharified product is glucose, the processes may further comprise isomerizing the glucose to fructose with a glucose (xylose) isomerase. See, for example, U.S. Pat. No. 5,935,837 and U.S. Pat. No. 4,687,742. An example of a commercially available xylose isomerase is SWEETZYME® (Novozymes A/S).

In another aspect, the present invention relates to processes for producing a fermentation product, comprising: (a) saccharifying a starch-containing material with an enzyme composition comprising one or more (several) amylolytic enzymes in the presence of a polypeptide having amylolytic enhancing activity of the present invention; and (b) fermenting the saccharified starch-containing material with one or more (several) fermenting microorganisms to produce a fermentation product. The presence of the polypeptide having amylolytic enhancing activity increases the saccharification of the starch-containing material compared to the absence of the polypeptide having amylolytic enhancing activity. In a preferred aspect, the processes further comprise (c) recovering the fermentation product from the fermentation.

In another aspect, the present invention relates to processes for producing a fermentation product from a starch-containing material, comprising: (a) liquefying the starch-containing material with an alpha-amylase; (b) saccharifying the liquefied starch-containing material with an enzyme composition comprising one or more (several) amylolytic enzymes; and (c) fermenting the saccharified starch-containing material in the presence of a fermenting organism; wherein step (a), step (b), or steps (a) and (b) are conducted in the presence of an effective amount of a polypeptide having amylolytic enhancing activity of the present invention. In a preferred aspect, the processes further comprise (d) recovering the fermentation product from the fermentation.

In the processes of the present invention, a polypeptide having amylolytic enhancing activity may be used in conjunction with one or more (several) amylolytic enzymes in a number of applications, such as those described below. Any suitable starch-containing starting material may be used. The starting material is generally selected based on the application and/or desired product.

High Fructose Corn Syrup. The conversion of starch to fructose can consist of four steps: liquefaction of granular starch, saccharification of the liquefied starch into dextrose, purification, and isomerization of the dextrose to fructose. Amylases are used to produce high MW dextrose syrups (oligosaccharides having a MW tightly grouped at about 20,000 MW). The fragments of approximately 20,000 MW can be rapidly and fully converted to glucose by glucoamylase and pullulanase. See, for example, WO 2004/091544.

Corn wet milling. Corn wet milling is a process that produces corn oil, gluten meal, gluten feed, and starch. Alkaline-amylase is used in the liquefaction of starch and glucoamylase is used in saccharification to produce glucose. An exemplary corn oil process comprises steeping, degerming, de-fibering and gluten separation, followed by liquefaction using, for example, an alpha-amylase, and saccharification using, for example, a glucoamylase. See, for example, WO 2004/091544.

Dry milling processes. In dry milling, whole grain is ground and combined with water. The germ is optionally removed by flotation separation or equivalent techniques. The resulting mixture, which contains starch, fiber, protein and other components of the grain, is liquefied using amylase. See, for example, WO 2004/091544.

Textile industry. Desizing removes size from textiles. After weaving a textile, the size coating must be removed before further processing the fabric in order to ensure a homogeneous and wash-proof result. Amylases are applied during or after the weaving of textiles, or during the desizing stage, or one or more (several) additional fabric processing steps. See, for example, U.S. Pat. No. 6,077,316.

Processes to produce homogenous maltodextrins. Amylases are involved in the process to produce homogenous maltodextrins. Homogenous maltodextrins can be used in a wide variety of food, drug and coating applications. The homogenous maltodextrins produced have a homogenous MW distribution and can be used in a variety of maltodextrin-comprising products, resulting in lower viscosity, clear (no haze) solutions, better coating properties, better film-forming properties, and the like. See, for example, WO 2004/091544.

Anti-staling processes of baked products. Staling of a baked product, e.g., bread, refers to changes undesirable to the consumer in the properties of the baked product, such as an increase of the firmness of the crumb, a decrease of the elasticity of the crumb, and changes in the crust, which becomes tough and leathery. Matogenic amylases are used to retard staling. See, for example, U.S. Pat. Nos. 6,197,352; 2,615,810 and 3,026,205; Silberstein, 1964, *Baker's Digest* 38: 66-72.

Corn fiber gum. High quality corn fiber gum can be produced by treatment of corn fiber with an amylase followed by hydrogen peroxide treatment to obtain an extract of milled corn fiber. See, for example, U.S. Pat. No. 6,147,206.

Animal feeds and additives. Treatment of animal feeds and additives with amylases can result in release of readily digestible and easily absorbed sugars, thereby increasing the digestive capacity of animals and birds. Amylase can be added as feed additives for animals or the animal feed can be treated with amylases prior to animal consumption. See, for example, WO 2004/091544.

Paper or pulp treatment. Amylases can be used to modify starch in pulp or paper thereby converting it into a liquefied form. See, for example, U.S. Pat. Nos. 6,241,849; 6,066,233; and 5,582,681. Amylases can also be used in the production of lignocellulosic materials such as pulp, paper and cardboard, and from starch reinforced waste paper and cardboard (amylases facilitate the disintegration of the waste material through degradation of the reinforcing starch). Amylases can be useful in a process for producing a paper-making pulp from starch-coated printed paper. See, for example, WO 95/14807.

Deinking of recycled paper pulp. Deinking processes involve disintegrating paper to produce a pulp, treating with a starch-degrading enzyme before, during, or after the disintegrating, and separating ink particles from the pulp after disintegrating and enzyme treatment. See, for example, U.S. Pat. No. 6,309,871.

Waste treatment. Amylases can be used in waste treatment. In a solid waste digestion process, the solid waste can be treated with amylases to reduce the mass and volume of the solid waste. See, for example, U.S. Pat. No. 5,709,796.

Oral care products. Amylases can be used in oral care products. Exemplary oral care products include toothpastes, dental creams, gels or tooth powders, odontics, mouth washes, pre- or post brushing rinse formulations, chewing gums, lozenges, or candy. See, for example, U.S. Pat. No. 6,264,925.

Drilling well and mining operations. Amylases can be used in well and drilling operations, e.g., gas, oil, etc. For example, amylases are used to increase the flow of production fluids from a subterranean formation and to remove viscous, starch-containing fluids that can be damaging to production operations. See, for example, U.S. Pat. No. 6,581,687.

Brewing. Amylases can be used in the process of brewing (e.g., fermenting) beer. Starch-containing raw materials are disintegrated and processed to form malt. The action of the amylase results in an increase in fermentable reducing sugars. See, for example, U.S. Pat. Nos. 5,762,991; 5,536, 650; 5,405,624; 5,021,246; 4,788,066.

Amylolytic Enzymes

In practicing the processes of the present invention, the one or more (several) amylolytic enzymes may be an alpha-amylase, an amyloglucosidase, a maltogenic alpha-amylase, a beta-amylase, a pullulanase, or combinations thereof.

Alpha-Amylases. The alpha-amylase may be any alpha-amylase useful in the processes of the present invention. In one aspect, the alpha-amylase is an acid alpha-amylase, e.g., a fungal acid alpha-amylase or a bacterial acid alpha-amylase. The term "acid alpha-amylase" means an alpha-amylase (E.C. 3.2.1.1) having optimal activity at a pH in the range of preferably 3 to 7, more preferably 3.5 to 6, and most preferably 4 to 5.

A bacterial alpha-amylase is preferably derived from the genus *Bacillus*. In a preferred aspect, the *Bacillus* alpha-amylase is derived from a strain of *B. licheniformis, B. amyloliquefaciens, B. subtilis* or *B. stearothermophilus*, but may also be derived from other *Bacillus* sp. Examples of alpha-amylases include *Bacillus licheniformis* alpha-amylase (WO 99/19467), *Bacillus amyloliquefaciens* alpha-amylase (WO 99/19467), and *Bacillus stearothermophilus* alpha-amylase (WO 99/19467). In another aspect, the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in WO 99/19467.

A *Bacillus* alpha-amylase may also be a variant and/or hybrid, such as the variants and hybrids disclosed in WO 96/23873, WO 96/23874, WO 97/41213, WO 99/19467, WO 00/60059, and WO 02/10355. Examples of other alpha-amylase variants are disclosed in U.S. Pat. Nos. 6,093,562, 6,297,038, and 6,187,576. The variants include *Bacillus stearothermophilus* alpha-amylase (BSG alpha-amylase) variants having a deletion of one or two amino acids at positions R179 to G182, preferably a double deletion disclosed in WO 1996/023873 (see, for example, page 20, lines 1-10), preferably corresponding to delta(181-182) compared to the wild-type BSG alpha-amylase amino acid sequence disclosed in WO 99/19467 or deletion of amino acids R179 and G180 according to WO 99/19467. Even more preferred are *Bacillus* alpha-amylases, especially *Bacillus stearothermophilus* alpha-amylases, which have a double deletion corresponding to delta(181-182) and further comprise a N193F substitution (also denoted I181*+G182*+N193F) compared to the wild-type BSG alpha-amylase disclosed in WO 99/19467.

The alpha-amylase may also be a hybrid alpha-amylase. In one aspect, the hybrid alpha-amylase comprises 445 C-terminal amino acid residues of the *Bacillus licheniformis* alpha-amylase (WO 99/19467) and the 37 N-terminal amino acid residues of the alpha-amylase derived from *Bacillus amyloliquefaciens* (WO 99/19467), with one or more (several), especially all, of the following substitutions: G48A+ T49I+G107A+H156Y+A181T+N190F+I201F+A209V+ Q264S (using the *Bacillus licheniformis* alpha-amylase numbering disclosed in WO 99/19467). Also preferred are variants having one or more (several) of the following mutations (or corresponding mutations in other *Bacillus* alpha-amylase backbones): H154Y, A181T, N190F, A209V, and Q264S and/or deletion of two residues between positions 176 and 179, preferably deletion of E178 and G179 (WO 99/19467).

Alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard. One Kilo Novo alpha amylase Unit (KNU) is defined as the amount of enzyme which, under standard conditions (i.e., at 37° C.+/− 0.05; 0.0003 M $Ca^{2+}$; and pH 5.6) dextrinizes 5260 mg starch dry substance Merck Amylum soluble. A folder EB-SM-0009.02/01 describing this analytical method is available upon request to Novozymes A/S, Denmark.

A bacterial alpha-amylase is dosed at an amount of 0.0005-5 KNU per g DS (dry solids), preferably 0.001-1 KNU per g DS, such as around 0.050 KNU per g DS.

The alpha-amylase may also be a fungal alpha-amylase. Fungal alpha-amylases include alpha-amylases obtained from strains of the genus *Aspergillus*, such as, *Aspergillus oryzae, Aspergillus niger* and *Aspergillus kawachii* alpha-amylases.

A preferred acidic alpha-amylase is obtained from a strain *Aspergillus niger*. In a preferred aspect, the acid fungal alpha-amylase is the alpha-amylase disclosed as "AMYA_ASPNG" in the Swiss-prot/TeEMBL database under the accession no. P56271 and described in WO 89/01969 (Example 3). A commercially available acid fungal alpha-amylase derived from *Aspergillus niger* is SP288 (available from Novozymes A/S, Denmark).

Other useful wild-type alpha-amylases include those obtained from strains of the genera *Rhizomucor* and *Meripilus*, preferably a strain of *Rhizomucor pusillus* (WO 2004/055178) or *Meripilus giganteus*.

In a preferred aspect the alpha-amylase is derived from *Aspergillus kawachii* disclosed by Kaneko et al., 1996, *J. Ferment. Bioeng.* 81: 292-298, and further as EMBL #AB008370.

The fungal alpha-amylase may also be a wild-type enzyme comprising a starch-binding domain (SBD) and an alpha-amylase catalytic domain (i.e., non-hybrid), or a variant thereof. In one aspect the wild-type alpha-amylase is derived from a strain of *Aspergillus kawachii*.

The alpha-amylase may also be a fungal hybrid alpha-amylase. Preferred examples of fungal hybrid alpha-amylases include those disclosed in WO 2005/003311, U.S. Patent Application 2005/0054071, or U.S. Patent Application No. 2006/0148054. A hybrid alpha-amylase may comprise an alpha-amylase catalytic domain (CD) and a carbohydrate-binding domain/module (CBM), such as a starch binding domain, and optionally a linker.

Specific examples of hybrid alpha-amylases include those disclosed in Tables 1-5 of U.S. Patent Application No. 2006/0148054, including an *Aspergillus oryzae* alpha-amylase variant with a catalytic domain JA118 and an *Athelia rolfsii* SBD (U.S. Patent Application No. 2006/0148054), *Rhizomucor pusillus* alpha-amylase with an *Athelia rolfsii* AMG linker and a SBD (U.S. Patent Application No. 2006/0148054), *Rhizomucor pusillus* alpha-amylase with an *Aspergillus niger* glucoamylase linker and a SBD (which is disclosed in Table 5 of U.S. Patent Application No. 2006/ 0148054) or as V039 in Table 5 of WO 2006/069290, and a *Meripilus giganteus* alpha-amylase with an *Athelia rolfsii* glucoamylase linker and a SBD (U.S. Patent Application No. 2006/0148054). Other useful hybrid alpha-amylases are those listed in Tables 3, 4, 5, and 6 in U.S. Patent Application No. 2006/0148054 and WO 2006/069290.

Other specific examples of hybrid alpha-amylases include those disclosed in U.S. Patent Application 2005/0054071, including those disclosed in Table 3 thereof, such as *Aspergillus niger* alpha-amylase with an *Aspergillus kawachii* linker and a starch binding domain.

Preferred commercial compositions comprising alpha-amylase include MYCOLASE™ from DSM (Gist Brocades); BAN™, TERMAMYL™ SC, FUNGAMYL™, LIQUOZYME™ X, SAN™ SUPER, and SAN™ EXTRA L (Novozymes A/S); CLARASE™ L-40,000, DEX-LO™, SPEZYME™ FRED, SPEZYME™ AA, SPEZYME™ DELTA AA, and SPEZYME XTRA™ (Genencor Int.); FUELZYME™ (Verenium Corp.); and the acid fungal alpha-amylase known as SP288 available from Novozymes A/S.

Acid alpha-amylase activity may be measured in AFAU (Acid Fungal Alpha-amylase Units), which are determined relative to an enzyme standard. One AFAU is defined as the amount of enzyme which degrades 5.260 mg starch dry matter per hour under standard conditions. A folder EB-SM-0259.02/01 describing this analytical method is available upon request to Novozymes A/S, Denmark.

Fungal Alpha-Amylase Units (FAU-F) are measured relative to an enzyme standard of a declared strength. A folder (EB-SM-0216.02) describing this standard method is available on request from Novozymes A/S, Denmark.

In the processes of the present invention, an acid alpha-amylase may be added in an amount of preferably 0.1 to 10 AFAU/g DS, more preferably 0.10 to 5 AFAU/g DS, and most preferably 0.3 to 2 AFAU/g DS or preferably 0.001 to 1 FAU-F/g DS and more preferably 0.01 to 1 FAU-F/g DS.

Glucoamylases. The glucoamylase may be any glucoamylase useful in the processes of the present invention. The glucoamylase may be obtained from any suitable source, e.g., a microorganism or a plant. Preferred glucoamylases are of fungal or bacterial origin. Examples of fungal glucoamylase are *Aspergillus* glucoamylases, in particular, *A. niger* G1 or G2 glucoamylase (Boel et al., 1984, *EMBO J.* 3: 1097-1102), or variants thereof, such as those disclosed in WO 92/00381, WO 00/04136 and WO 01/04273; *A. awamori* glucoamylase disclosed in WO 84/02921, *A. oryzae* glucoamylase (Hata et al., 1991, *Agric. Biol. Chem.* 55: 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues at position A435 and S436 (Li et al., 1997, *Protein Eng.* 10: 1199-1204).

Other useful glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50:323-330), *Talaromyces* glucoamylases, in particular, glucoamylases obtained from *Talaromyces emersonii* (WO 99/28448), *Talaromyces leycettanus* (U.S. Pat. No. Re. 32,153), *Talaromyces duponti*, and *Talaromyces thermophilus* (U.S. Pat. No. 4,587,215).

Other useful bacterial glucoamylases include glucoamylases from the genus *Clostridium*, in particular *C. thermoamylolyticum* (EP 135,138), and *C. thermohydrosulfuricum* (WO 86/01831), and *Trametes cingulata* disclosed in WO 2006/069289.

Also hybrid glucoamylases can be used in the processes of the present invention. Examples of hybrid glucoamylases are disclosed in WO 2005/045018. Specific examples include the hybrid glucoamylases disclosed in Tables 1 and 4 of Example 1 (which hybrids are hereby incorporated by reference).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME ULTRA™, and AMG™ E (from Novozymes A/S); OPTIDEX™ 300, GC480™ and GC147™ (from Genencor Int.); AMIGASE™ and AMIGASE™ PLUS (from DSM); and G-ZYME™ G900, G-ZYME™ and G990 ZR (from Genencor).

The Novo Glucoamylase Unit (AGU) is defined as the amount of enzyme, which hydrolyzes 1 micromole of maltose per minute under standard conditions of 37° C., pH 4.3, using 23.2 mM maltose as substrate in 0.1 M acetate buffer for a reaction time of 5 minutes. An autoanalyzer system may be used where mutarotase is added to the glucose dehydrogenase reagent so that any alpha-D-glucose present is converted to beta-D-glucose. Glucose dehydrogenase reacts specifically with beta-D-glucose in the reaction mentioned above, forming NADH which is determined at 340 nm as a measure of the original glucose concentration. A folder (EB-SM-0131.02/01) describing this analytical method is available on request from Novozymes A/S, Denmark.

Glucoamylases are preferably added in an amount of 0.0001-20 AGU/g DS, more preferably 0.001-10 AGU/g DS, 0.02-10 AGU/g DS, more preferably 0.1-10 AGU/g DS, even more preferably 0.1-5 AGU/g DS, and most preferably 0.1-2 AGU/g DS, even.

Beta-Amylases. The beta-amylase may be any beta-amylase useful in the processes of the present invention. Beta-amylases have been isolated from various plants and microorganisms (W. M. Fogarty and C. T. Kelly, 1979, *Progress in Industrial Microbiology* 15: 112-115). These beta-amylases are characterized by having optimum temperatures in the range from 40° C. to 65° C. and optimum pH in the range from 4.5 to 7. Commercially available beta-amylases are NOVOZYM™ WBA from Novozymes A/S, Denmark and SPEZYME™ BBA 1500 from Genencor Int., USA.

A beta-amylase Unit (BAMU) is defined as the amount of enzyme that degrades one µmole of maltohexose per minute, or defined as the activity presented by 1 mg of pure beta-amylase enzyme. One BAMU is defined relative to the BAMU of an enzyme standard. A folder (EB-SM-0516.02/01) describing this analytical method is available on request from Novozymes A/S, Denmark.

Maltogenic alpha-amylases. The maltogenic alpha-amylase may be any maltogenic alpha-amylase useful in the processes of the present invention. Maltogenic alpha-amylases (glucan 1,4-alpha-maltohydrolase, E.C. 3.2.1.133) hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628.

One MANU (Maltogenic Amylase Novo Unit) is defined as the amount of enzyme required to release one micromole of maltose per minute at a concentration of 10 mg of maltotriose (Sigma M 8378; Sigma Chemical Co., St. Louis, Mo., USA) substrate per ml of 0.1 M citrate pH 5.0 buffer at 37° C. for 30 minutes.

The maltogenic amylase is preferably added in an amount of 0.05-5 mg total protein/gram DS or 0.05-5 MANU/g DS.

Pullulanases. The pullulanase may be any pullulanase useful in the processes of the present invention. Pullulanases (E.C. 3.2.1.41), also known as pullulanan-6-glucanohydrolase, degrade alpha-1,6-linkages of pullulan, amylopectin, and other branched substrates. In the grain industry, bacterial pullulanases have been used for the purpose of removing alpha-1,6 bonds in starch, which may cause undesirable panose formation in the saccharification process.

A number of bacterial pullulanases are known. Kelly et al., 1994, *FEMS Microbiology Letters* 115: 97-106 describe the pullulanase B gene of *Bacillus acidopullulyticus*. WO 96/35794 describes a pullulanase from *Bacillus* sp.

Examples of commercial pullulanase products that can be used in the methods of the present invention include, but are not limited to, DEXTROZYME®, PROMOZYME® D2, and ATTENUZYME® from Novozymes A/S.

Pullulanase activity may be determined relative to a pullulan substrate. Pullulan is a linear D-glucose polymer consisting essentially of maltotriosyl units joined by 1,6-alpha-links. Endo-pullulanases hydrolyze the 1,6-alpha-links at random, releasing maltotriose, $6^3$-alpha-maltotriosyl-maltotriose, $6^3$-alpha-($6^3$-alpha-maltotriosyl-maltotriosyl)-maltotriose. One New Pullulanase Unit Novo (NPUN) is a unit of endo-pullulanase activity and is measured relative to a Novozymes A/S PROMOZYME® standard. Standard conditions are 30 minutes reaction time at 40° C. and pH 4.5; and with 0.7% pullulan as substrate. The amount of red substrate degradation product is measured spectrophotometrically at 510 nm and is proportional to the endo-pullulanase activity in the sample. One NPUN equals the amount of enzyme which under the standard conditions liberates reducing carbohydrate with a reducing power equivalent to 2.86 micromole glucose per minute.

The pullulanase is preferably added in an amount of 0.05-5 NPUN/g DS.

In the methods of the present invention, the polypeptide having amylolytic enhancing activity and other amylolytic protein(s) may be supplemented by one or more (several) additional enzyme activities to improve the degradation of the starch-containing material. Preferred additional enzymes are cellulases, hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

In the processes of the present invention, the optimum amounts of a polypeptide having amylolytic enhancing activity and amylolytic enzyme(s) depend on several factors including, but not limited to, the mixture of amylolytic enzymes, the starch-containing material, the concentration of starch-containing material, temperature, time, and pH.

In one aspect, the amount of polypeptide having amylolytic enhancing activity per g of starch-containing material is preferably about 0.01 to about 50 mg, more preferably about 0.1 to about 20 mg, and most preferably about 1 to about 10 mg per g of starch-containing material.

In another aspect, the amount of polypeptide having amylolytic enhancing activity per g of amylolytic enzyme(s) is preferably about 0.005 to about 20 g, more preferably about 0.05 to about 20 g, and most preferably about 0.5 to about 10 g per g of amylolytic enzyme(s).

Fermentation

The fermentable sugars obtained from the starch-containing material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the starch-containing material as a result enzymatic hydrolysis, are fermented to a fermentation product by a fermenting organism, such as yeast. The fermentation can also be carried out simultaneously with the enzymatic saccharification in the same vessel, again under controlled pH, temperature, and mixing conditions. When saccharification and fermentation are performed simultaneously in the same vessel, the process is generally termed simultaneous saccharification and fermentation or SSF.

Any suitable starch-containing material may be used in a fermentation process of the present invention. The substrate is generally selected based on the desired fermentation product, i.e., the fermentation product to be obtained from the fermentation, and the process employed, as is well known in the art.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms are able to ferment, i.e., convert, sugars, such as glucose, maltose, or maltodextrins directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment C6 sugars include bacterial and fungal organisms, such as yeast. Preferred yeast includes strains of the *Saccharomyces* spp., preferably *Saccharomyces cerevisiae*.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMO-SACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

The fermenting microorganism is typically added to the degraded starch-containing material or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded starch-containing material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 18 of SEQ ID NO: 2, amino acids 1 to 18 of SEQ ID NO: 4, or amino acids 1 to 18 of SEQ ID NO: 6. In a preferred aspect, the isolated polynucleotide encoding a signal peptide comprises or consists of nucleotides 1 to 54 of SEQ ID NO: 1, nucleotides 1 to 54 of SEQ ID NO: 3, or nucleotides 1 to 54 of SEQ ID NO: 5.

The present invention also relates to nucleic acid constructs comprising a gene encoding a protein, wherein the gene is operably linked to the isolated polynucleotide encoding the signal peptide, wherein the gene is foreign to the polynucleotide encoding the signal peptide.

The present invention also relates to recombinant expression vectors and recombinant host cells comprising such nucleic acid constructs.

The present invention also relates to methods of producing a protein, comprising: (a) cultivating a recombinant host cell comprising a gene encoding a protein operably linked to the such a polynucleotide encoding a signal peptide, wherein the gene is foreign to the polynucleotide under conditions conducive for production of the protein; and (b) recovering the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Chemicals used as buffers and substrates were commercial products of at least reagent grade.

Strains

*Aspergillus oryzae* JaL250 strain (WO 99/61651) was used for expression of the *Neurospora crassa* polypeptide having amylolytic enhancing activity. *Aspergillus oryzae* JaL355 strain (WO 2005/070962) was used for expression of the *Aspergillus nidulans* polypeptide having amylolytic enhancing activity. *Aspergillus oryzae* BECh2 strain (WO 2000/039322) was used for expression of the *Aspergillus oryzae* polypeptide having amylolytic enhancing activity.

Media

PDA plates were composed of 39 grams of potato dextrose agar and deionized water to 1 liter.

Minimal medium+sucrose plates were composed per liter of 6 g of $NaNO_3$, 0.52 g of KCl, 1.52 g $KH_2PO_4$, 1 ml of COVE trace elements solution, and 342.3 g sucrose; the pH was adjusted to 6.5 with a 1N NaOH solution and then 20 g of Agar Noble were added. The suspension was then autoclaved and allowed to cool down to 55° C. before adding 20 ml of a 50% glucose solution, 20 ml of 0.02% biotin solution, and 2.5 ml of a 20% $MgSO_4.7H_2O$ solution before making the plates.

COVE trace elements solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4H_2O$, 0.8 g of $Na_2MoO_2.2H_2O$, 10 g of $ZnSO_4.7H_2O$, and deionized water to 1 liter.

MDU2BP medium was composed of 45 g of maltose, 1 g of $MgSO_4.7H_2O$, 1 g of NaCl, 2 g of $K_2HSO_4$, 12 g of $KH_2PO_4$, 2 g of urea, 500 µl of AMG trace metals solution, and deionized water to 1 liter; the pH was adjusted to 5.0 and then filter sterilized with a 0.22 µm filtering unit.

YPM medium was composed of 10 g of yeast extract, 20 of g Bacto peptone, 20 g of maltose, and deionized water to 1 liter.

YP medium was composed of 10 g yeast extract, 20 g Bacto peptone, and deionized water to 1 liter.

YEG medium was composed of 5 g of yeast extract, 20 g of dextrose, and deionized water to 1 liter.

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, 3 g of citric acid, and deionized water to 1 liter.

SOC medium was composed of 2% tryptone, 0.5% yeast extract, 10 mM NaCl, 2.5 mM KCl, 10 mM $MgCl_2$, and 10 mM $MgSO_4$; sterilized by autoclaving and then filter-sterilized glucose was added to 20 mM.

STC was composed of 1 M sorbitol, 50 mM Tris-HCl pH 6.5, and 50 mM $CaCl_2$.

PEG solution was composed of 50% (w/v) PEG 4000, 50 mM Tris-HCl pH 6.5, and 50 mM $CaCl_2$.

COVE selection medium was composed of 342.3 g of sucrose, 20 ml of COVE salts solution, 10 mM acetamide, 0.03 M CsCl, 30 g of Noble agar, and deionized water to 1 liter.

COVE top agarose was composed of 342.3 g of sucrose, 20 ml of COVE salts solution, 10 mM acetamide, 0.03 M CsCl, 10 g of low melt agarose, and deionized water to 1 liter.

COVE-2 was composed of 30 g of sucrose, 20 ml of COVE salts solution, 10 mM acetamide, 30 g of Noble agar, and deionized water to 1 liter.

COVE salts solution was composed of 26 g of KCl, 26 g of $MgSO_4$, 76 g of $KH_2PO_4$, 50 ml of COVE trace metals solution, and deionized water to 1 liter.

COVE-N-gly was composed of 218 g of sorbitol, 10 g of glycerol, 2.02 g of $KNO_3$, 50 ml of COVE salts solution, 25 g of agar BA10, and deionized water to 1 liter.

MLC medium was composed of 40 g of glucose, 50 g of soy bean powder, 4 g of citric acid, a few drops of pluronic acid, and deionized water to 1 liter; the pH was adjusted to 5.0.

MSS medium was composed of 70 g of glucose, 100 g of soy bean powder, a few drops of pluronic acid, and deionized water to 1 liter; the pH was adjusted to 6.0.

MU-1 medium was composed of 260 g of malt dextrin, 3 g of $MgSO_4.7H_2O$, 6 g of $K_2SO_4$, 5 g of $KH_2PO_4$, a few drops of pluronic acid, and deionized water to 1 liter; the pH was adjusted to 4.5.

MU1-MLC/MSS was a mix of 1000 ml of MU-1 medium, 40 ml of 50% urea, 100 ml of MLC medium, and 100 ml of MSS medium.

M410 medium was composed of 50 g of glucose, 50 g of maltose, 2 g of $MgSO_47H_20$, 2 g of $KH_2PO_4$, 4 g of citric acid, 8 g of yeast extract, 2 g of urea, 0.5 g of $CaCl_2$, 0.5 ml of AMG trace metals solution, and deionized water to 1 liter; pH to 6.0 with sodium hydroxide; filter sterile through 0.22 µm membrane.

Example 1

Isolation of Genomic DNA from *Neurospora crassa* and *Aspergillus nidulans*

*Neurospora crassa* was obtained from the Fungal Genetics Stock Center (Kansas City, Mo., USA) as FGSC 2489 and maintained on PDA plates. One hundred ml of YEG medium in a 500 ml flask were inoculated with an agarose plug from a PDA plate and grown for 2 days at 34° C. with shaking at 200 rpm. Biomass was harvested onto a Nalgene 281-5000 glass fiber prefilter (Thermo Fisher Scientific, Rochester, N.Y., USA), rinsed extensively with 10 mM Tris-0.1 mM EDTA pH 7.4 (TE), frozen in liquid nitrogen, and ground to a powder with a mortar and pestle. A few grams of powder were suspended in 20 ml of 20 mM CAPS-NaOH pH 11.0, 0.5% LDS, 1 mM EDTA and incubated at 60° C. for 60 minutes with periodic mixing by inversion. An equal volume of neutralized phenol:chloroform (1:1) was added and extraction was continued for 2 hours at room 37° C. with continuous mixing on a Belly Dancer shaker (Fotodyne Incorporated, Hartland Wis., USA). After centrifugation at 1300×g for 10 minutes in a swinging bucket rotor, the aqueous phase was removed and re-extracted by brief shaking with neutralized phenol:chloroform (1:1). Centrifugation was repeated and the aqueous phase was brought to 2.5 M ammonium acetate, frozen, thawed, and centrifuged at 13,000×g for 20 minutes at 6° C. To the supernatant was added a 0.7 volume of isopropanol and the precipitated nucleic acids were pelleted by centrifugation at 17,000×g for 20 minutes. The resulting pellet was rinsed twice with 70% ethanol, air dried, and dissolved in 1.0 ml of 0.1×TE. RNA was digested by addition of 100 µg of RNase A (Promega, Madison, Wis., USA) and incubation at room temperature for 30 minutes. DNA was precipitated and pelleted by addition of ammonium acetate to 2.0 M and 2 volumes of ethanol followed by centrifugation at 13,000×g for 15 minutes. The pellet was rinsed twice with 70% ethanol, air dried, and dissolved in 0.75 ml of 0.1×TE.

*Aspergillus nidulans* wild-type strain was obtained from the Fungal Genetics Stock Center (FGSC A1000; Kansas City, Mo., USA) and maintained on PDA plates. One hundred ml of YEG medium in a 500 ml flask were inoculated with an agarose plug from a PDA plate and grown for 2 days at 37° C. with shaking at 200 rpm. Biomass was harvested onto a Nalgene 281-5000 glass fiber prefilter, rinsed extensively with TE, frozen in liquid nitrogen, and ground to a powder with a mortar and pestle. A few grams of powder were suspended in 30 ml of 10 mM CAPS-NaOH pH 11.0, 0.5% LDS, 1 mM EDTA, split into two 50 ml centrifuge tubes, and incubated at 60° C. for 30 minutes with periodic mixing by inversion. An equal volume of neutralized phenol:chloroform (1:1) was added and extraction was continued overnight at room temperature with continuous mixing on a Belly Dancer shaker. After centrifugation at 1300×g for 10 minutes in a swinging bucket rotor, the aqueous phase was removed and re-extracted by brief shaking with neutralized phenol:chloroform (1:1). Centrifugation was repeated and the aqueous phase was brought to 2.5 M ammonium acetate, frozen, thawed, and centrifuged at 13,000×g for 20 minutes at 6° C. To the supernatant was added a 0.8 volume of isopropanol and the precipitated nucleic acids were pelleted by centrifugation at 17,000×g for 20 minutes at room temperature. The resulting pellet was rinsed three times with 70% ethanol, air dried, and dissolved in 2.0 ml of 0.5×TE. RNA was digested by addition of 100 µg of RNase A and incubation at 37° C. for 30 minutes. DNA was precipitated by addition of ammonium acetate to 2.0 M and 2 volumes of ethanol followed by centrifugation at 13,000×g for 15 minutes at 4° C. The pellet was rinsed three times with 70% ethanol, air dried, and dissolved in 0.5 ml of 0.1×TE. When fully dissolved, KCl was added to a final concentration of 20 mM.

Example 2

Cloning of a *Neurospora crassa* Polypeptide Having Amylolytic Enhancing Activity Gene (aepA)

Based upon a predicted gene in the *Neurospora crassa* genome sequence (gene name B24N4.140), two synthetic oligonucleotide primers shown below were designed to PCR amplify a *Neurospora crassa* aepA gene from the genomic DNA prepared in Example 1. An IN-FUSION™ PCR Cloning Kit (BD Biosciences, Palo Alto, Calif., USA) was used to clone the fragment directly into the expression vector pAlLo2 (WO 2004/099228) without the need for restriction digestion and ligation.

```
NCB24N4140 Sense:
                                        (SEQ ID NO: 7)
5'-ACTGGATTTACCATGAAGTTCTCCATCATCTCGGTT-3'

NCB24N4140 anti:
                                        (SEQ ID NO: 8)
5'-TCACCTCTAGTTAATTAACTACTTCCACGACGACTCAA-3'
```

Bold letters represent coding sequence. The remaining sequence is homologous to the insertion sites of pAlLo2.

Thirty picomoles of each of the primers above were used in an amplification reaction containing 400 ng of *Neurospora crassa* genomic DNA, 1×Pfx Amplification Buffer (Invitrogen, Carlsbad, Calif., USA), 1.7 µl of a 10 mM blend of dATP, dTTP, dGTP, and dCTP, 2.5 units of PLATINUM® Pfx DNA Polymerase (Invitrogen, Carlsbad, Calif., USA), and 1 µl of 50 mM MgSO$_4$ in a final volume of 50 µl. The amplification reaction was incubated in an EPPENDORF® MASTERCYCLER® 5333 (Eppendorf Scientific, Inc., Westbury, N.Y., USA) programmed for 1 cycle at 96° C. for 3 minutes; and 33 cycles each at 94° C. for 50 seconds, 60° C. for 50 seconds, and 68° C. for 2 minutes. The heat block then went to a 4° C. soak cycle.

The reaction products were isolated by 1.2% agarose gel electrophoresis using 40 mM Tris base-20 mM sodium acetate-1 mM disodium EDTA (TAE) buffer where a 1.3 kb product band was excised from the gel and purified using a QIAQUICK® Gel Extraction Kit (QIAGEN Inc., Valencia, Calif., USA) according to the manufacturer's instructions.

The fragment was then cloned into the pAlLo2 expression vector using an IN-FUSION™ PCR Cloning Kit. The vector was digested with Nco I and Pac I. The fragment was purified by gel electrophoresis and a QIAQUICK® Gel Extraction Kit as above. The gene fragment and the digested vector were incubated together in a reaction resulting in the expression plasmid pPH48 (FIG. 1) in which transcription of the aepA gene was under the control of a NA2-tpi promoter (a modified promoter including the gene encoding neutral alpha-amylase in *Aspergillus niger* in which the untranslated leader has been replaced by an untranslated leader from the gene encoding triose phosphate isomerase in *Aspergillus nidulans*). The IN-FUSION™ reaction (50 µl) was composed of 1×IN-FUSION™ Buffer (BD Biosciences, Palo Alto, Calif., USA), 1×BSA (BD Biosciences, Palo Alto, Calif., USA), 1 µl of IN-FUSION™ enzyme (diluted 1:10) (BD Biosciences, Palo Alto, Calif., USA), 150 ng of pAlLo2 digested with Nco I and Pac I, and 50 ng of the *Neurospora crassa* aepA purified PCR product. The reaction was incubated at room temperature for 30 minutes. One µl of the reaction was used to transform *E. coli* XL10 SOLOPACK® Gold cells (Stratagene, La Jolla, Calif., USA). An *E. coli* transformant containing the pPH48 plasmid was detected by restriction digestion analysis and plasmid DNA was prepared using a BIOROBOT® 9600 (QIAGEN Inc., Valencia, Calif., USA).

Example 3

Characterization of the *Neurospora crassa* Polypeptide Having Amylolytic Enhancing Activity Gene (aepA)

DNA sequencing of the 1.3 kb PCR fragment was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, *Journal of Virology Methods* 38: 47-60). The following vector primers were used for sequencing:

```
795(TPI)fw
                                        (SEQ ID NO: 9)
5'-CCACACTTCTCTTCCTTCCTC-3'

796rv:
                                        (SEQ ID NO: 10)
5'-CCCCATCCTTTAACTATAGCG-3'
```

Nucleotide sequence data were scrutinized for quality and all sequences were compared to each other with assistance of PHRED/PHRAP software (University of Washington, Seattle, Wash., USA). The sequence was compared and aligned with the original database sequence (EMBL ID CAE75704) and was a 100% match.

A gene model for the *Neurospora crassa* genomic DNA sequence was constructed based on similarity of the encoded protein to homologous predicted proteins in the public databases. The nucleotide sequence (SEQ ID NO: 1) and deduced amino acid sequence (SEQ ID NO: 2) of the *N. crassa* genomic DNA sequence are shown in FIGS. 2A and 2B. The genomic fragment of 1276 bp (including stop codon) encodes a polypeptide of 385 amino acids, interrupted by 2 introns of 58 and 60 bp. The % G+C content of the gene and the mature coding sequence are 57.4% and 59.1%, respectively. A starch-binding domain (carbohydrate-binding module family 20, Prosite accession number PS51166) was present from approximately residues 278 to 385 of the pre-polypeptide. Using the SignalP software program (Nielsen et al., 1997, *Protein Engineering* 10:1-6), a signal peptide of 18 residues was predicted. The predicted mature protein contains 367 amino acids with a predicted molecular mass of 39.2 kDa and a pI of 5.1.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Neurospora crassa* gene encoding the mature polypeptide having amylolytic enhancing activity shared 99.7% and 97.8% identity (excluding gaps) to the deduced amino acid sequences of two predicted hypothetical polypeptides from *Neurospora crassa* (UniProt Accession numbers Q6MWQ3 and Q7SCE9, respectively). Both of these are alternate (and probably incorrect) gene models for the same gene sequence as aepA. The next most related protein is a predicted hypothetical polypeptide from *Aspergillus clavatus* (Uniprot Accession number A1CN59) with 71.6% identity.

Example 4

Expression of the *Neurospora crassa* Polypeptide Having Amylolytic Enhancing Activity (AepA) in *Aspergillus oryzae* JaL250

*Aspergillus oryzae* Jal250 (WO 99/61651) protoplasts were prepared according to the method of Christensen et al., 1988, *Bio/Technology* 6: 1419-1422. A total of 2.71 µg of pPH48 was used to transform the *Aspergillus oryzae* JaL250 protoplasts.

The transformation of *Aspergillus oryzae* JaL250 with pPH48 (Example 2) yielded about 50 transformants. Eight transformants were isolated to individual PDA plates and incubated for five days at 34° C.

Confluent spore plates were washed with 3 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, a 1.5 ml aliquot of each culture was collected and centrifuged at 12,000×g. A 7.5 µl sample of each supernatant was mixed with an equal volume of 2× loading buffer (10% beta-mercaptoethanol) and loaded onto a 1.5 mm 8%-16% Tris-Glycine SDS-PAGE gel and stained with SIMPLYBLUE™ Safe Stain (Invitrogen, Carlsbad, Calif., USA). SDS-PAGE profiles of the culture broths showed that seven out of eight transformants had a new protein band of approximately 50 kDa. The apparent molecular weight of the new protein band is about 10 kDa larger that the predicted molecular weight of 39.2 kDa. This size differential may be due to post-translational modifications like glycosylation. Transformant number 2 was selected for further studies and designated *Aspergillus oryzae* JaL250PH48. Subsequent experiments demonstrated that expression of the AepA protein in this strain was higher in YPM medium, and this medium was used for subsequent expression.

Example 5

Cloning of an *Aspergillus nidulans* Polypeptide Having Amylolytic Enhancing Activity Gene (aepA)

Based upon a predicted gene in the *Aspergillus nidulans* genome sequence (gene name AN5463.2), two synthetic oligonucleotide primers shown below were designed to PCR amplify an *Aspergillus nidulans* aepA gene from genomic DNA prepared in Example 1. An IN-FUSION™ PCR Cloning Kit was used to clone the fragment directly into the expression vector pAlLo2 without the need for restriction digestion and ligation.

```
AN5463 Sense:
                                      (SEQ ID NO: 11)
5'-ACTGGATTTACCATGAAGTCTCTCCTCGCCCTTGTG-3'

AN5463 anti:
                                      (SEQ ID NO: 12)
5'-TCACCTCTAGTTAATTAACTACCGCCATGCACCACTCT-3'
```

Bold letters represent coding sequence. The remaining sequence is homologous to the insertion sites of pAlLo2.

Thirty picomoles of each of the primers above were used in an amplification reaction containing 400 ng of *Aspergillus nidulans* genomic DNA, 1× Pfx Amplification Buffer, 1.7 µl of a 10 mM blend of dATP, dTTP, dGTP, and dCTP, 2.5 units of PLATINUM® Pfx DNA Polymerase, and 1 µl of 50 mM MgSO$_4$ in a final volume of 50 µl. The amplification reaction was incubated in an EPPENDORF® MASTERCYCLER® 5333 programmed for 1 cycle at 96° C. for 3 minutes; and 33 cycles each at 94° C. for 50 seconds, 60° C. for 50 seconds, and 68° C. for 2 minutes. The heat block then went to a 4° C. soak cycle.

The reaction products were isolated by 1.2% agarose gel electrophoresis using TAE buffer where a 1.2 kb product band was excised from the gel and purified using a QIAQUICK® Gel Extraction Kit according to the manufacturer's instructions.

Figure 3:
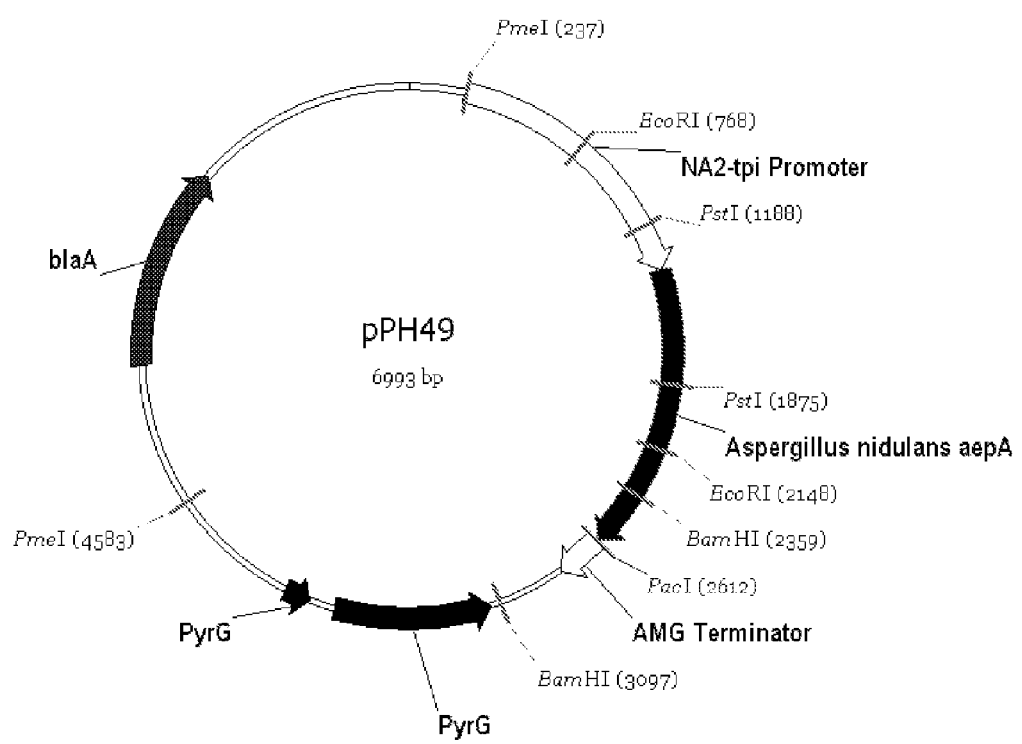
FIG. 3 shows a restriction map of pPH49.

The fragment was then cloned into pAlLo2 using an IN-FUSION™ PCR Cloning Kit. The vector was digested with Nco I and Pac I. The fragment was purified by gel electrophoresis and a QIAQUICK® Gel Extraction Kit as above. The gene fragment and the digested vector were incubated together in a reaction resulting in the expression plasmid pPH49 (FIG. 3) in which transcription of the aepA gene was under the control of a NA2-tpi promoter (a modified promoter including the gene encoding neutral alpha-amylase in *Aspergillus niger* in which the untranslated leader has been replaced by an untranslated leader from the gene encoding triose phosphate isomerase in *Aspergillus nidulans*). The IN-FUSION™ reaction (50 µl) was composed of 1×IN-FUSION™ Buffer, 1×BSA, 1 µl of IN-FUSION™ enzyme (diluted 1:10), 150 ng of pAlLo2 digested with Nco I and Pac I, and 50 ng of the *Aspergillus nidulans* aepA purified PCR product. The reaction was incubated at room temperature for 30 minutes. One µl of the reaction was used to transform *E. coli* XL10 SOLOPACK® Gold cells. An *E. coli* transformant containing the pPH49 plasmid was detected by restriction digestion and plasmid DNA was prepared using a BIOROBOT®9600.

Example 6

Characterization of the *Aspergillus nidulans* Polypeptide Having Amylolytic Enhancing Activity Gene (aepA)

DNA sequencing of the 1.2 kb PCR fragment was performed as described in Example 3. The 1.2 kb sequence was compared and aligned with the original database sequence (GenBank Accession number NT_107010) and was a 100% match.

A gene model for the *Aspergillus nidulans* genomic DNA sequence was constructed based on the predicted gene model for this DNA sequence (UniProt Accession Number Q5B1W7). The nucleotide sequence (SEQ ID NO: 3) and deduced amino acid sequence (SEQ ID NO: 4) of the *A. nidulans* genomic DNA sequence are shown in FIGS. 4A and 4B. The genomic fragment of 1217 bp (including stop codon) encodes a polypeptide of 385 amino acids, interrupted by one intron of 59 bp. The % G+C content of the gene and the mature coding sequence are 53.3% and 53.8%, respectively. A starch-binding domain (carbohydrate-binding module family 20, Prosite accession number PS51166) was present from approximately residues 278 to 385 of the pre-polypeptide. Using the SignalP software program (Nielsen et al., 1997, supra), a signal peptide of 18 residues was predicted. The predicted mature protein contains 367 amino acids with a predicted molecular mass of 39.1 kDa and a pI of 4.5.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Aspergillus nidulans* gene encoding the mature polypeptide having amylolytic enhancing activity shared 100% and 80.0% identity (excluding gaps) to the deduced amino acid sequences of two predicted hypothetical polypeptides from *Aspergillus nidulans* and *Neosartorya fischeri* (UniProt Accession numbers Q5B1W7 and A1D1F9, respectively).

Example 7

Expression of the *Aspergillus nidulans* Polypeptide Having Amylolytic Enhancing Activity (AepA) in *Aspergillus oryzae* JaL355

*Aspergillus oryzae* JaL355 protoplasts were prepared according to the method of Christensen et al., 1988, supra. The *Aspergillus oryzae* JaL355 protoplasts were transformed with 2.71 µg of pPH49 (described in Example 5).

The transformation of *Aspergillus oryzae* JaL355 with pPH49 yielded about 40 transformants. Eight transformants were isolated to individual PDA plates and incubated for five days at 34° C.

Confluent spore plates were washed with 3 ml of 0.01% TWEEN® 80 in MDU2BP medium and the spore suspension was used to inoculate 25 ml of MDU2BP medium in 125 ml glass shake flasks. Transformant cultures were incubated at 34° C. with constant shaking at 200 rpm. At day five post-inoculation, a 1.5 ml aliquot of each culture was collected and centrifuged at 12,000×g. A 7.5 µl sample of each supernatant was mixed with an equal volume of 2× loading buffer (10% R-mercaptoethanol) and loaded onto a 1.5 mm 8%-16% Tris-Glycine SDS-PAGE gel and stained with SIMPLYBLUE™ Safe Stain.

SDS-PAGE profiles of the culture broths showed that seven of the eight transformants produced a new protein band of approximately 55 kDa. The apparent molecular weight of the new protein band was about 14 kDa larger than the predicted molecular weight of 39.1 kDa. This size differential may be due to post-translational modifications like glycosylation. Transformant number 5 was selected for further studies and designated *Aspergillus oryzae* Jal250PH49 clone #5.

Example 8

Single-Spore Isolation of *Aspergillus oryzae* JaL355PH49 Clone #5

To insure genotype homogeneity and to determine whether a pure isolate could produce more recombinant *Aspergillus nidulans* polypeptide having amylolytic enhancing activity (AepA), single-spore cultures were generated from the original *Aspergillus oryzae* Jal250PH49 clone #5. Two hundred microliters of 0.01% TWEEN® 80 in MDU2BP medium were added to a small area of a confluent spore plate of *Aspergillus oryzae* Jal250PH49 clone #5. The spores in this area were re-suspended with a sterile Arber spreader (Arber Bioscience, Rochester, N.Y., USA) so that the re-suspended area was not larger than 13 mm in diameter. A 100 µl aliquot of the spore suspension was collected and diluted in 5 ml of 0.01% TWEEN® 80 solution. The spore concentration was determined employing a hemocytometer (Hausser Scientific, Horsham, Pa., USA) by counting 5 of the $0.2^2$ mm squares of the central square millimeter (four corners plus center one) on each side of the chamber. The average value of these counts was determined and multiplied by 5 to determine the total number of spores per square millimeter and then multiplied by $10^4$ to obtain the number of spores per microliter. The spores were then diluted in 0.01% TWEEN® 80 in MDU2BP medium to a final concentration of 0.1 spores per microliter. Three hundred microliters of the spore suspension containing 30 spores were plated onto 150 mm Minimal medium+sucrose plates and incubated for 2 to 3 days at 34° C. Once the colonies were clearly visible, 10 colonies were selected at random and transferred individually to 100 mm PDA plates and incubated for five days at 34° C.

Example 9

Analysis of Expression of *Aspergillus oryzae* JaL355PH49 clone #5 Single-Spore Isolates Confluent spore plates from all ten single-spore isolates of *Aspergillus oryzae* JaL355PH49 clone #5 were washed with 3 ml of 0.01% TWEEN® 80 in MDU2BP medium and the spore suspension was used to inoculate 25 ml of MDU2BP medium in 125 ml glass shake flasks. Transformant cultures were incubated at 34° C. with constant shaking at 200 rpm. At day five post-inoculation, a 1.5 ml aliquot of each culture was collected and centrifuged at 12,000×g. A 7.5 µl sample of each supernatant was mixed with an equal volume of 2× loading buffer (10% beta-mercaptoethanol) and loaded onto a 1.5 mm 8%-16% Tris-Glycine SDS-PAGE gel and stained with SIMPLYBLUE™ Safe Stain.

SDS-PAGE profiles of the culture broths showed that all ten transformants had a protein pattern similar to the original *Aspergillus oryzae* JaL355PH49 clone #5. Four out of the ten had a more intense protein band of approximately 55 kDa suggesting that these isolates were capable of producing more *Aspergillus nidulans* AepA. From these four isolates, isolate #8 was selected for further studies and designated *Aspergillus oryzae* JaL355PH49.

Example 10

Large Shake Flask Cultures of the *Neurospora crassa* Polypeptide Having Amylolytic Enhancing Activity Expressed in *Aspergillus oryzae* Jal250PH48

*Aspergillus oryzae* Jal250PH48 spores were spread onto a PDA plate and incubated for five days at 34° C. The confluent spore plate was washed twice with 5 ml of 0.01% TWEEN® 20 to maximize the number of spores collected. The spore suspension was then used to inoculate 100 ml of YPM medium in a 500 ml flask. The transformant culture was incubated at 34° C. with constant shaking at 200 rpm. At day four post-inoculation, the culture broth was collected by filtration through a 0.22 μm EXPRESS™ Plus Membrane (Millipore, Bedford, Mass., USA). A 5 μl sample of the broth was analyzed by SDS-PAGE as described above to confirm that the protein pattern was the same as the one obtained before. Once the broth was shown to contain the expected protein band of approximately 55 kDa by SDS-PAGE, the broth was submitted for purification and enzymatic characterization.

Example 11

Large Shake Flask Cultures of the *Aspergillus nidulans* Polypeptide Having Amylolytic Enhancing Activity Expressed in *Aspergillus oryzae* JaL355PH49

*Aspergillus oryzae* JaL250PH49 spores were spread onto a PDA plate and incubated for five days at 34° C. Culture broth was generated as described in Example 10.

Example 12

Construction of pHUda666 Expression Vector for *Trametes cingulata* Amyloglucosidase The gene encoding an amyloglucosidase from *Trametes cingulata* was cloned from genomic DNA and subsequently subcloned into an expression vector and transformed into *Aspergillus oryzae* as described in WO 2006/069289. The resulting *A. oryzae* expression strain NC000651 was fermented in shake flasks for 3 days with maltose as the sole carbon source in order to induce expression of the gene. Mycelia were harvested and total RNA was isolated using an RNEASY® Mini Kit (QIAGEN Inc., Valencia, Calif., USA). cDNA for the amyloglucosidase gene was synthesized using a 3' RACE system (Invitrogen, Carlsbad, Calif., USA) following the manufacturer's protocol and the primers shown below.

```
Forward primer:
                              (SEQ ID NO: 13)
5'-tttggatccaccatgcgtttcacgctcctcacc-3'

Reverse primer:
                              (SEQ ID NO: 14)
5'-tttctcgagctaccgccaggtgtcgttctg-3'
```

Figure 5:
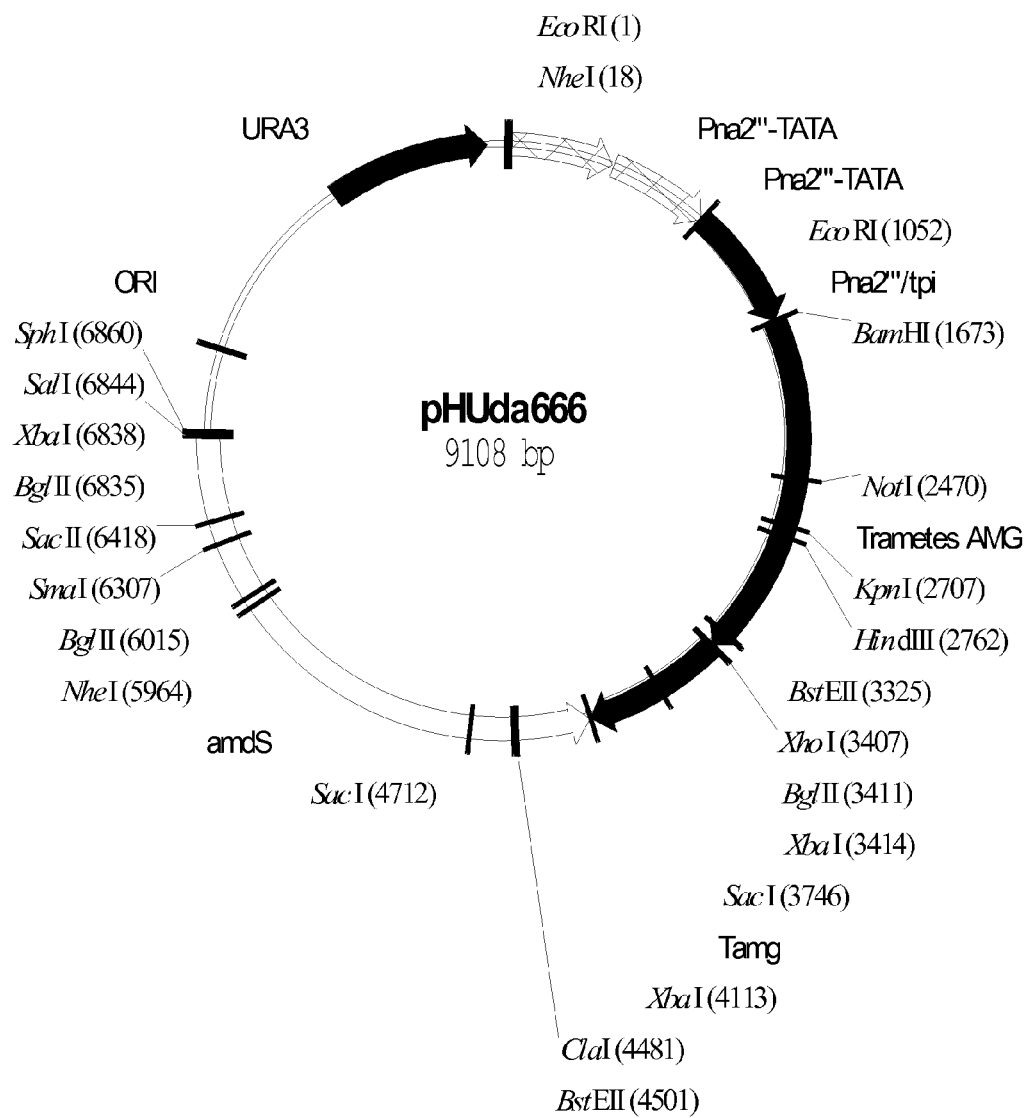
FIG. 5 shows a restriction map of pHUda666.

The amplified 1.7 kb fragment was digested with Bam HI and Xho I and ligated into a Bam HI and Xho I site of plasmid pT7Blue (Invitrogen, Carlsbad, Calif., USA). The ligation mixture was then transformed into *E. coli* DH12α (Invitrogen, Carlsbad, Calif., USA). Plasmid DNA samples were prepared for sequencing using a QIAPREP® Spin Miniprep Kit (QIAGEN Inc., Valencia, Calif., USA) according to the manufacturer's instructions. A single clone harboring a plasmid containing the *Trametes cingulata* amyloglucosidase cDNA gene was isolated. The insert was excised by digestion with Bam HI and Xho I and ligated into Bam HI and Xho I-digested pJaL790 (WO 2007/045248). A single clone harboring a plasmid containing the *Trametes cingulata* amyloglucosidase cDNA gene was isolated and designated pHUda666 (FIG. 5).

Example 13

Expression of *Trametes cingulata* Amyloglucosidase Expressed in *Aspergillus niger*

*Aspergillus niger* strain BO1 was inoculated into 25 ml of YP medium containing 2% glucose and 1 M sucrose and grown overnight at 30° C. with shaking at 150 rpm. Mycelia were collected by filtration through a 0.2 μm STERICUP EXPRESS™ Plus membrane (Millipore Corporation, Billerica, Mass., USA, rinsed with 250 ml of 1 M sorbitol, and filtered again. Mycelia were suspended in 30 ml of 1 M sorbitol containing per ml 20 mg of GLUCANEX® 200 G (Novozymes A/S, Bagsvaerd, Denmark) and 0.33 mg of chitinase (Sigma, St. Louis, Mo., USA) in a 125 ml flask and incubated at 34° C. for 45 minutes at 100 rpm. The solution was cooled on ice, filtered through two layers of MIRA-CLOTH® (Calbiochem, La Jolla, Calif., USA), diluted up to 50 ml with 1 M sorbitol, and centrifuged for 5 minutes at 1500 rpm in a Sorvall 7500 swinging bucket rotor. The pellet was resuspended in 1 M sorbitol and the centrifugation and resuspension repeated three times. The final pellet was suspended in STC:PEG solution:DMSO (2.7:0.5:0.035) at a concentration of $3 \times 10^7$ protoplasts per ml and stored at −80° C. For transformation, 5-10 μg of pHUda666 plasmid DNA was mixed with an equal volume of heparin solution (5 mg per ml of 50 mM $CaCl_2$-1.2 M sorbitol) and 100 μl of protoplasts prepared as described above. The solution was gently mixed and incubated on ice for 20 minutes. One ml of 40% PEG 4000, 0.8 M sorbitol, 50 mM $CaCl_2$ was added and the solution was incubated for 20 minutes at room temperature. Then 7-10 ml of COVE top agarose at 50° C. was added and the solution was poured onto a plate of COVE selection medium, allowed to harden, and incubated at 34° C. for 3-7 days. Fifty transformants from each strain were subcultured to COVE-2 medium and single colony isolates were transferred to COVE-N-gly medium and incubated at 32° C. for approximately 3 weeks. Spores were collected in 3-5 ml of 0.01% TWEEN® 20 and frozen in 10% glycerol. The spore suspensions were subsequently thawed and 40 μl of each suspension were inoculated into 4 ml of MU1-MLC/MSS medium in a 14 ml round-bottom tube and incubated at 30° C. for up to 10 days at 200 rpm. Culture supernatants were analyzed by SDS-PAGE for expression of an approximately 70 kDa band. The top transformant (CKIe43) was chosen for scale-up fermentation.

Shake flask medium was composed per liter of 70 g of sucrose and 100 g of soy concentrate. One hundred ml of shake flask medium was added to a 500 ml shake flask. The shake flask was inoculated with 300 μl from a glycerol spore stock and incubated at 30° C. on an orbital shaker at 220 rpm for 72 hours. Fifty ml of the shake flask broth from each of four separate shake flasks was used to inoculate a 3 liter fermentation vessel.

Fermentation batch medium was composed of 50 g of maltodextrin, 8.5 g of $(NH_4)_2SO_4$, 2 g of $KH_2PO_4$, 2 g of $MgSO_4.7H_2O$, 3 g of $K_2SO_4$, 0.8 g $Na_2HPO_4$, 1.1 g of citric acid, 0.5 ml of anti-foam, 1 ml of trace metals solution #1, 0.5 ml of trace metals solution #2, and deionized water to 1 liter. The trace metals solution #1 was composed of 13.8 g of $FeSO_4.7H_2O$, 14.3 g of $ZnSO_4.7H_2O$, 11.6 g of $MnSO_4.H_2O$, 2.5 g of $CuSO_4.5H_2O$, 0.5 g of $NiCl_2.6H_2O$, 3.3 g of citric acid monohydrate, and deionized water to 1 liter. The trace metals solution #2 was composed of 400 g of $CaCl_2.2H_2O$, 10 g of $NaNO_3$, and deionized water to 1 liter. Fermentation feed medium was composed per kilogram of 690 g of glucose, 1.5 g of citric acid monohydrate, 0.9 ml of trace metals solution #2, and 1 ml of anti-foam.

A total of 2 liters of the fermentation batch medium was added to an Applikon Biotechnology two liter glass jacketed fermentor (Applikon Biotechnology, Schiedam, Netherlands). Fermentation feed medium was dosed at a rate of 0 to 5.4 g/l/hr for a period of 185 hours. The fermentation vessel was maintained at a temperature of 34° C. and pH was controlled using an Applikon 1010 control system (Applikon Biotechnology, Schiedam, Netherlands) to a set-point of 4.85+/−0.1. Air was added to the vessel at a rate of 1.2 vvm and the broth was agitated by Rushton impeller rotating at 1100 rpm. After 8 days, whole broth was harvested from the vessel and centrifuged at 3000×g to remove the biomass. The supernatant was sterile filtered and stored at 5 to 10° C.

Example 14

Purification of *Neurospora crassa* Polypeptide Having Amylolytic Enhancing Activity Broth supernatant containing *Neurospora crassa* polypeptide having amylolytic enhancing activity, obtained according to Example 10, was desalted by loading 50 ml of the broth supernatant onto 4 serially connected HIPREP® 26/10 columns (GE Healthcare Life Sciences, Piscataway, N.J., USA), with each column having a volume of 13 ml, and then eluting with 20 mM Tris pH 8.0. Fractions of 8 ml were collected, and fractions 1-8 were pooled based on SDS-PAGE analysis of the fractions using an 8-16% Tris-HCl gel (Bio-Rad Laboratories, Inc., Hercules, Calif., USA). The pooled fractions were then further purified using a 20 ml MonoQ HIPREP® 16/10 column (GE Healthcare Life Sciences, Piscataway, N.J., USA). A 50 ml volume of the pooled fractions was loaded onto the MonoQ HIPREP® 16/10 column and then eluted using a 20 column volume gradient from 0 to 0.25 M NaCl in 20 mM Tris-HCl pH 8.0. Fractions of 5 ml were collected, and fractions 33 through 37 were submitted to SDS-PAGE analysis. SDS-PAGE on an 8-16% Tris-HCl gel with Coomassie blue staining showed the samples to be greater than 95% pure.

Example 15

Effect of the *Neurospora crassa* Polypeptide Having Amylolytic Enhancing Activity in the Hydrolysis of Amylopectin The *Neurospora crassa* polypeptide having amylolytic enhancing activity was evaluated for its ability to enhance the hydrolysis of amylopectin by *Aspergillus niger* acid alpha-amylase and *Trametes cingulata* amyloglucosidase, each alone and in combination. Hydrolysis of amylopectin was conducted with 5 g of amylopectin (Sigma Chemical Co., St. Louis, Mo., USA; Sigma A8515, lot 102k3775) per liter of 1.75 mM $CaCl_2$-50 mM sodium citrate pH 4.0. *Trametes cingulata* amyloglucosidase was added at 1.3 mg per liter final protein concentration. *Aspergillus niger* acid alpha-amylase (Novozymes A/S, Bagsvaerd, Denmark; SP288), dissolved at a concentration of 10 g per liter of 50 mM sodium citrate pH 4.0 buffer, was added at 20 mg per liter final protein concentration. The hydrolytic reactions were incubated at room temperature overnight with or without 7.6 mg of the *Neurospora crassa* polypeptide having amylolytic enhancing activity per liter. For each reaction, a single reaction mixture of 800 µl was prepared and then aliquoted in triplicate at 200 µl per well in a 1 ml deep well plate (Axygen Scientific, Union City, Calif., USA; #P-DW-11-C, lot 080102-112). Glucose standards at 100, 75, 50, 25, 12.5 and 0 mg per liter of 50 mM sodium citrate pH 4.0 buffer were added in duplicate at 200 µl per well. The plate was then heat sealed using an ALPS-300 plate sealer (ABgene, Rochester, N.Y., USA) and left overnight at room temperature.

After overnight incubation, the plate was assayed for reducing sugar concentration using a PHBAH (4-hydroxybenzhydride) assay. Fifty microliters of 0.5 M NaOH were added to each well of the plate (including glucose standards) to stop the reactions. The amylopectin containing samples were diluted 40-fold into diluent composed of one part of 0.5 M NaOH with 4 parts of 50 mM sodium citrate pH 4.0 buffer by mixing 12.5 µl of sample with 87.5 µl of the diluent, followed by mixing 20 µl of the 8-fold diluted sample with 80 µl of the diluent. Both dilutions were prepared in Thermowell V-bottom 96-well plates (Corning, Inc., Oneonta, N.Y., USA; Corning #6511). A 100 µl sample of each glucose standard (with NaOH) was added to wells of the final dilution plate, and then 50 µl of 1.5% (w/v) PHBAH (Sigma H9882, lot #054k1344) in 0.5 M NaOH were added to each well. The plate was then heated at 95° C. on an Omega CN76000 heating block (AmeriTechnology Group, Inc., Sacramento, Calif., USA) for 10 minutes. After heating, 50 µl of deionized water were added to each well, and 100 µl of each sample were transferred to a clear, flat-bottom 96-well plate (Corning, Inc., Oneonta, N.Y., USA; Corning #9017). The absorbance at 410 nm was then measured using a SPECTRAMAX® 340 pc spectrophotometric plate reader (Molecular Devices, Sunnyvale, Calif., USA). Glucose concentration was determined from a straight-line fit to the concentration of glucose versus the absorbance at 410 nm for the glucose standards.

Figure 6:
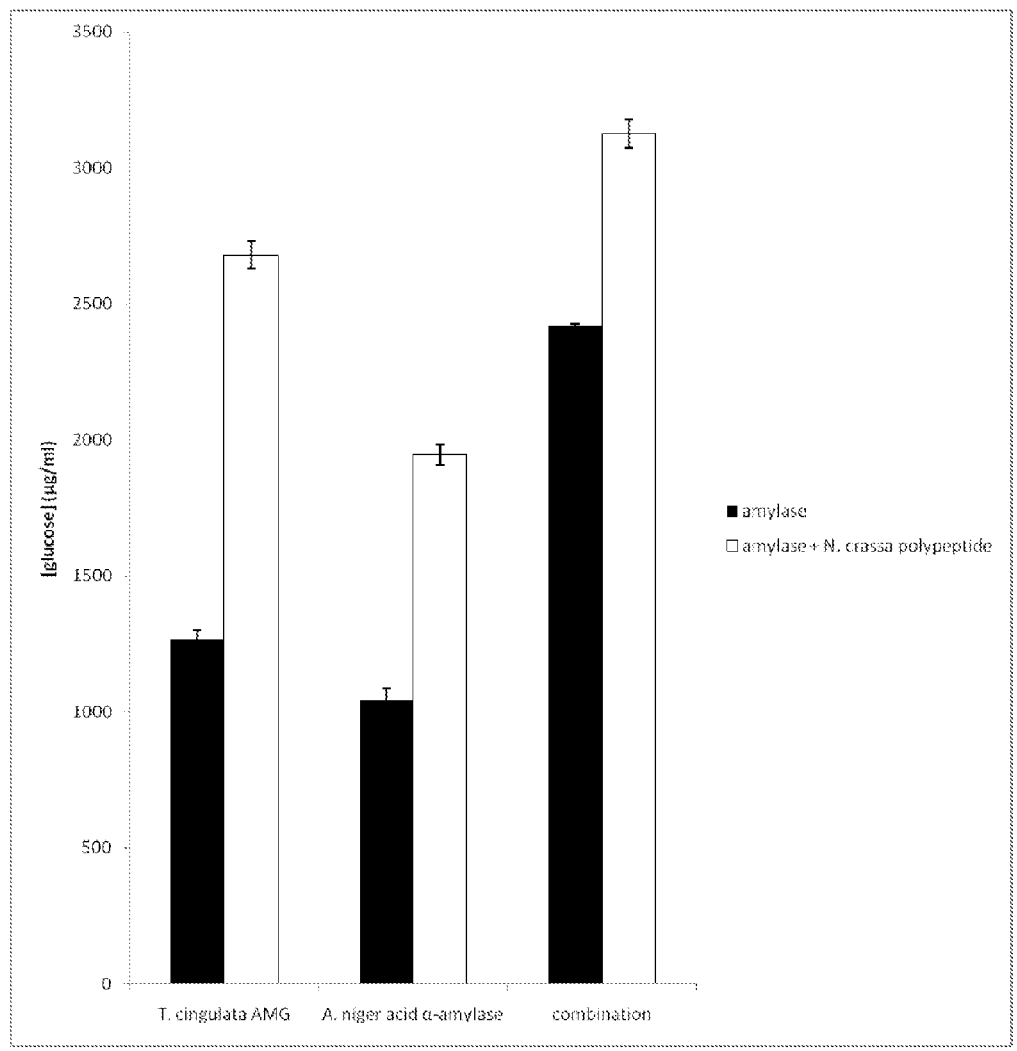
FIG. 6 shows the effect of the *Neurospora crassa* polypeptide having amylolytic enhancing activity on the hydrolysis of amylopectin by *Trametes cingulata* amyloglucosidase, *Aspergillus niger* acid alpha-amylase, and a combination of the *T. cingulata* amyloglucosidase and the *A. niger* acid alpha-amylase at pH 4.0 and room temperature.

The results shown in FIG. 6 demonstrated that the *Neurospora crassa* polypeptide having amylolytic enhancing activity enhanced hydrolysis of amylopectin by the *Trametes cingulata* amyloglucosidase, the *Aspergillus niger* acid alpha-amylase, and a combination of the amyloglucosidase and the alpha-amylase. The polypeptide having amylolytic enhancing activity alone produced no measurable hydrolysis of amylopectin.

Example 16

Purification of *Aspergillus nidulans* Polypeptide Having Amylolytic Enhancing Activity Broth supernatant containing *Aspergillus nidulans* polypeptide having amylolytic enhancing activity, obtained according to Example 11, was desalted by loading 50 ml of the broth supernatant onto 4 serially connected HIPREP® 26/10 columns, with each column having a volume of 13 ml, and then eluting with 20 mM Tris HCl pH 8.0. Fractions of 8 ml were collected, and fractions 3-8 were pooled based on SDS-PAGE analysis of the fractions using an 8-16% Tris-HCl gel. The pooled fractions were then further purified using a 20 ml MonoQ HIPREP® 16/10 column. A 48 ml volume of the pooled fractions was loaded onto the MonoQ HIPREP® 16/10 column and then eluted using a 20 column volume gradient from 0 to 0.5 M NaCl in 20 mM Tris-HCl pH 8.0. Fractions of 5 ml were collected, and fractions 50 and 53 through 59 were submitted to SDS-PAGE analysis. SDS-PAGE on an 8-16% Tris-HCl gel with Coomassie blue staining showed the samples to be greater than 95% pure.

Example 17

Effect of the *Aspergillus nidulans* Polypeptide Having Amylolytic Enhancing Activity and *Neurospora crassa* Polypeptide Having Amylolytic Enhancing Activity in the Hydrolysis of Amylose The *Aspergillus nidulans* and *Neurospora crassa* polypeptides having amylolytic enhancing activity were evaluated for their ability to enhance the hydrolysis of amylose by *Bacillus licheniformis* alpha-amylase (Novozymes A/S, Bagsvaerd, Denmark, TERMAMYL™ standard, batch 19-1197). Hydrolysis of amylose was conducted with 5 g of amylose type III from potato (Sigma Chemical Co., St. Louis, Mo., USA) per liter of 1.75 mM $CaCl_2$-50 mM sodium citrate pH 4.0 or 1.75 mM $CaCl_2$-50 mM sodium citrate pH 6.0. The amylose was essentially free of amylopectin. The *Bacillus licheniformis* alpha-amylase, dissolved at a concentration of 5 g per liter of 50 mM Tris HCl pH 8.0 buffer, was added at 20 mg per liter final protein concentration. The hydrolytic reactions were incubated at room temperature overnight with or without 7.6 mg of *Neurospora crassa* polypeptide having amylolytic enhancing activity or 3.6 mg of *Aspergillus nidulans* polypeptide having amylolytic enhancing activity per liter. For each reaction, a single reaction mixture of 1300 µl was prepared and then aliquoted in triplicate at 125 µl per well in three AXYGEN® 1 ml deep well plates. For the pH 4.0 plate, glucose standards at 100, 75, 50, 25, 12.5, and 0 mg per liter of 50 mM sodium citrate pH 4.0 buffer were added in duplicate at 125 µl per well. For the pH 6.0 plate, glucose standards at 100, 75, 50, 25, 12.5 and 0 mg per liter of 50 mM sodium citrate pH 6.0 buffer were added in duplicate at 125 µl per well. The plates were then heat sealed using an ALPS-300 plate sealer and left overnight at room temperature, 40° C., or 50° C.

After overnight incubation, the plates were assayed for reducing sugar concentration using the PHBAH assay described in Example 15, except 31.3 µl of 0.5 M NaOH were added to each well of the plate (including glucose standards) to stop the reactions; and amylose containing samples were diluted 20-fold into diluent composed of one part of 0.5 M NaOH with 4 parts of 50 mM sodium citrate pH 4.0 buffer by mixing 5 µl of sample with 95 µl of the diluent.

Figure 7:
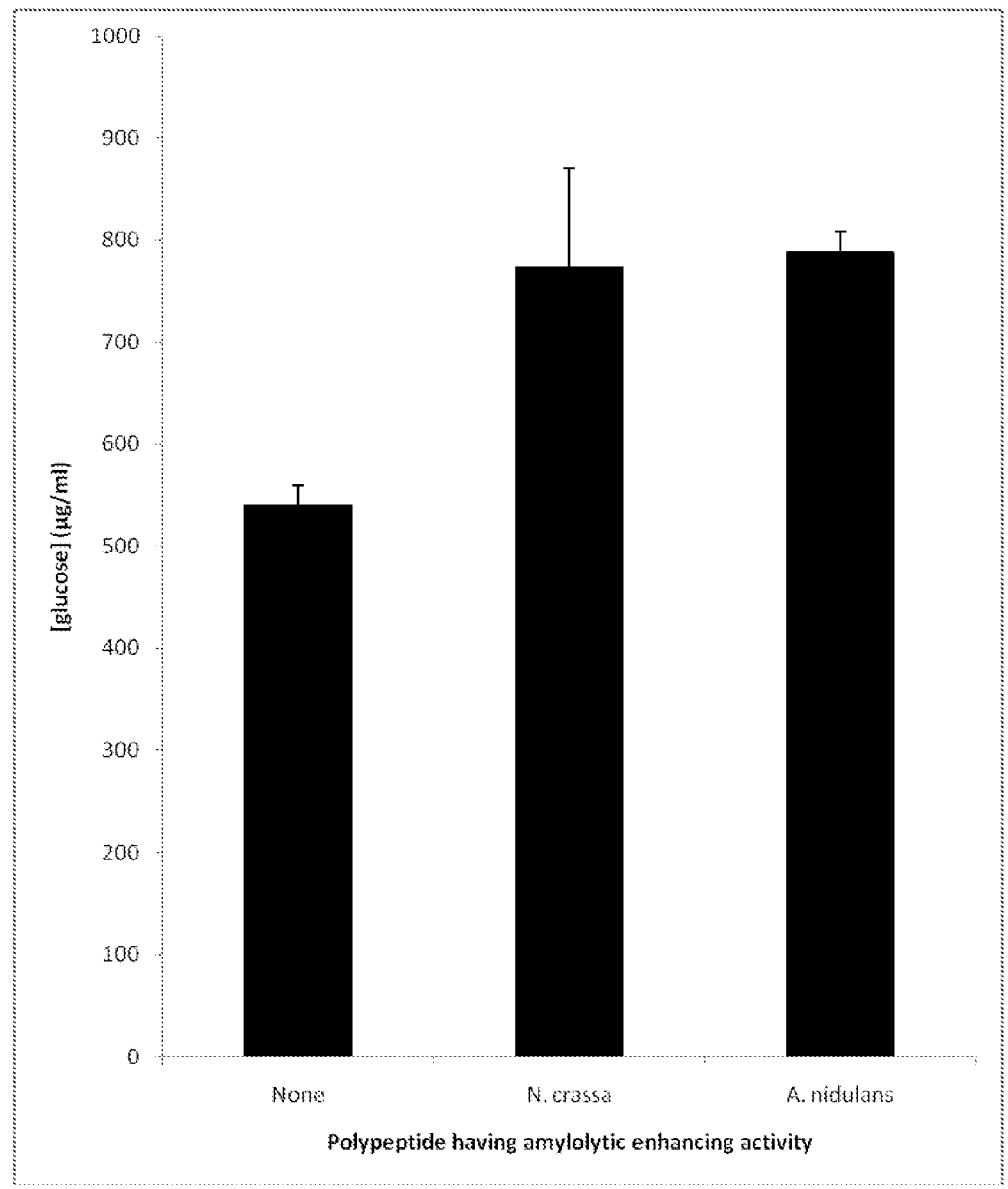
FIG. 7 shows the effect of the *Aspergillus nidulans* and *Neurospora crassa* polypeptides having amylolytic enhancing activity on the hydrolysis of amylose by *Bacillus licheniformis* alpha-amylase at pH 6.0 and room temperature.
Figure 8:
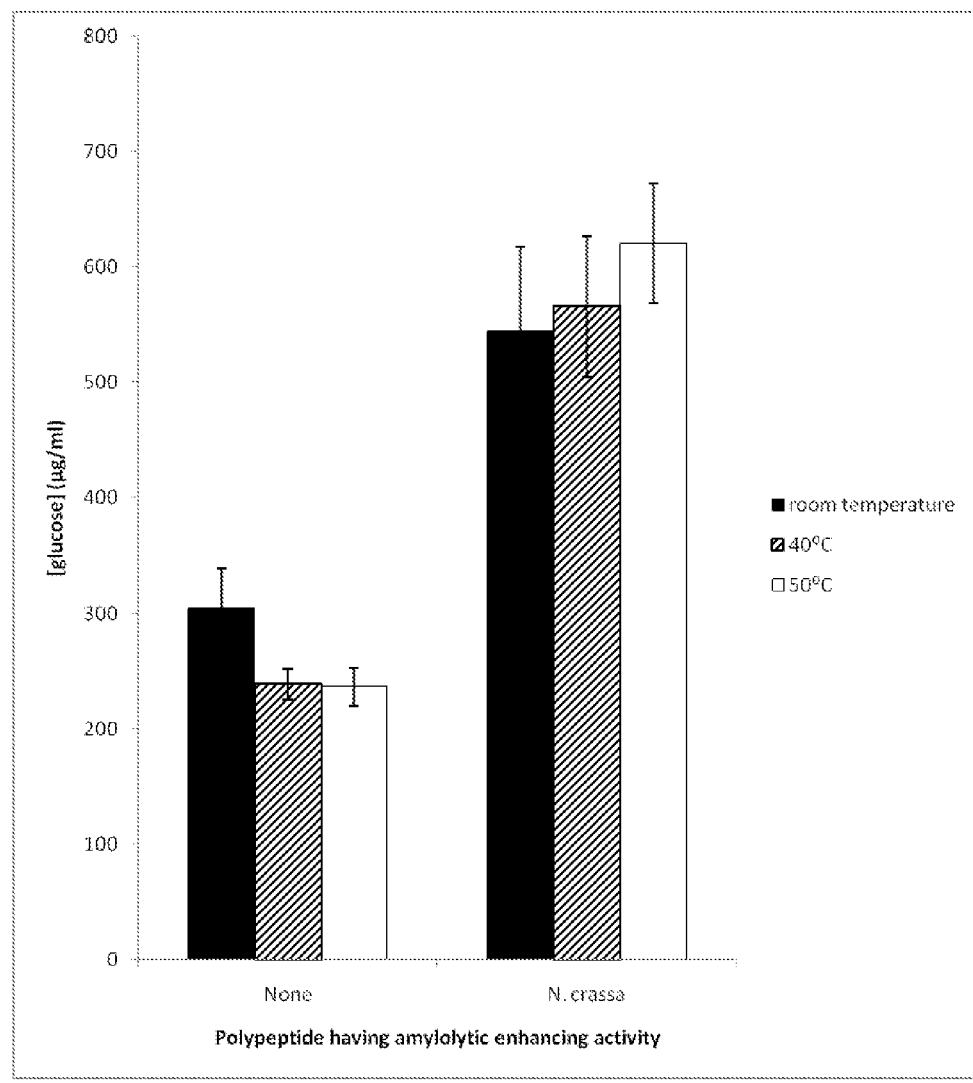
FIG. 8 shows the effect of the *Neurospora crassa* polypeptide having amylolytic enhancing activity on the hydrolysis of amylose by *Bacillus licheniformis* alpha-amylase at pH 4.0 and either room temperature, 40° C., or 50° C.

The results shown in FIG. 7 demonstrated that the polypeptides having amylolytic enhancing activity from both *Aspergillus nidulans* and *Neurospora crassa* enhanced hydrolysis of amylose by *Bacillus licheniformis* alpha-amylase at pH 6.0 and room temperature. The results shown in FIG. 8 demonstrated that the polypeptide having amylolytic enhancing activity from *Neurospora crassa* enhanced hydrolysis of amylose by the *Bacillus licheniformis* alpha-amylase at pH 4.0 and room temperature, 40° C., and 50° C.

Example 18

Effect of the *Aspergillus nidulans* and *Neurospora crassa* Polypeptides Having Amylolytic Enhancing Activity in the Hydrolysis of Amylopectin with *Talaromyces emersonii* and *Trametes cingulata* Amyloglucosidases

*Aspergillus nidulans* and *Neurospora crassa* polypeptides having amylolytic enhancing activity were evaluated for their ability to enhance the hydrolysis of amylopectin by *Trametes cingulata* amyloglucosidase or *Talaromyces emersonii* amyloglucosidase. Hydrolysis of amylopectin was conducted with 5 g of amylopectin per liter of 1.75 mM $CaCl_2$-50 mM sodium citrate pH 5.0. *Trametes cingulata* amyloglucosidase, obtained as described in Example 13, was added at 1.3 mg per liter final protein concentration. *T. emersonii* amyloglucosidase (Novozymes A/S, Bagsvaerd, Denmark; SPIRIZYME® Fuel, batch NAP00204) was diluted 8.250-fold into 1.75 mM $CaCl_2$-50 mM sodium citrate pH 5.0, and then further diluted 20-fold into the final reaction mixture. The hydrolytic reactions were incubated at room temperature overnight with or without 7.6 mg of *Neurospora crassa* or *Aspergillus nidulans* polypeptide having amylolytic enhancing activity per liter. For each reaction, a single reaction mixture of 800 µl was prepared and then aliquoted in triplicate at 200 µl per well in an AXYGEN® 1 ml deep well plate. Glucose standards at 100, 75, 50, 25, 12.5 and 0 mg per liter of 50 mM sodium citrate pH 5.0 buffer were added in duplicate at 200 µl per well. The plate was then sealed with a silicone 96 well plate cap (Nalgene, Rochester, N.Y., USA) and left overnight at room temperature.

After overnight incubation, the plate was assayed for reducing sugar concentration using the PHBAH assay described in Example 15.

Figure 9:
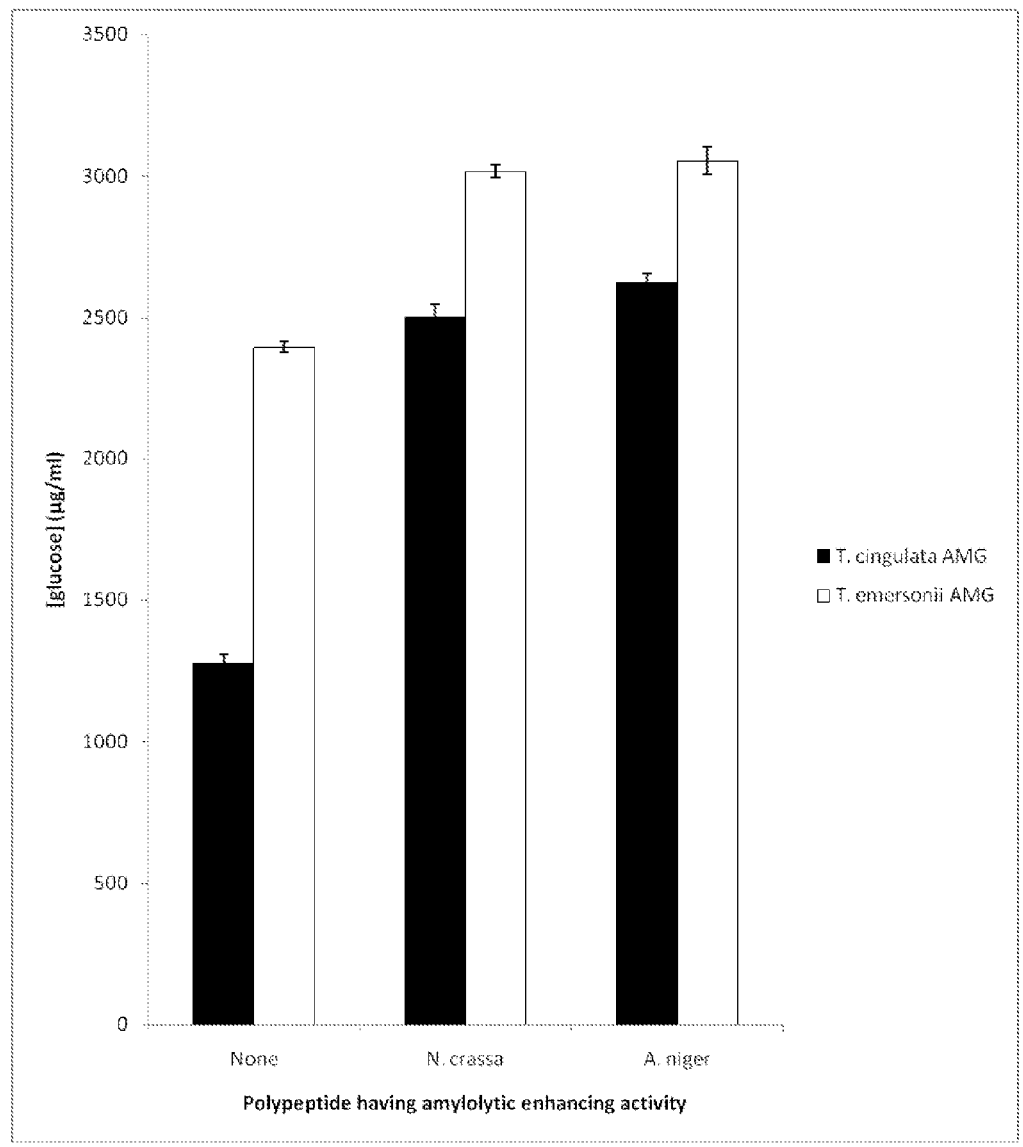
FIG. 9 shows the effect of the *Neurospora crassa* and *Aspergillus nidulans* polypeptides having amylolytic enhancing activity on the hydrolysis of amylopectin by *Trametes cingulata* amyloglucosidase and *Talaromyces emersonii* amyloglucosidase at pH 5.0 and room temperature.

The results shown in FIG. 9 demonstrated that each of the polypeptides having amylolytic enhancing activity from *Neurospora crassa* and *Aspergillus nidulans* enhanced hydrolysis of amylopectin by *Trametes cingulata* amyloglucosidase and by *Talaromyces emersonii* amyloglucosidase.

Example 19

Effect of the *Aspergillus nidulans* Polypeptide Having Amylolytic Enhancing Activity on the Hydrolysis of Corn Starch The *Aspergillus nidulans* polypeptide having amylolytic enhancing activity was evaluated for its ability to enhance the hydrolysis of corn starch by *Trametes cingulata* amyloglucosidase. Hydrolysis of corn starch was conducted with 50 g of corn starch (Sigma Chemical Co., St. Louis, Mo., USA) per liter of 1.75 mM $CaCl_2$-50 mM sodium citrate pH 5.0. *Trametes cingulata* amyloglucosidase, obtained as described in Example 13, was added at 2.0 mg per liter final protein concentration. The hydrolytic reactions were incubated at room temperature overnight with or without 10 mg of *Aspergillus nidulans* polypeptide having amylolytic enhancing activity per liter. For each reaction, a single reaction mixture of 800 µl was prepared and then aliquoted in triplicate at 200 µl per well in an AXYGEN® 1 ml deep well plate. Glucose standards at 1000, 500, 250, 125, 62.5 and 0 mg per liter of 50 mM sodium citrate pH 5.0 buffer were added in duplicate at 200 µl per well. The plate was then heat sealed using an ALPS-300 plate sealer and left overnight at room temperature.

After overnight incubation, the plate was assayed for glucose using a glucose oxidase assay. One hundred microliters of 0.5 M NaOH were added to each well of the plate (including glucose standards) to stop the reactions. Then 20 µl from each well were transferred to a clear, flat-bottom 96-well plate containing 200 µl per well liquid glucose oxidase reagent (Pointe Scientific, Canton, Mich., USA, #G7521, lot #815601-182) and incubated for 7 minutes at room temperature. The absorbance at 490 nm was then measured using a SPECTRAMAX® 340 pc spectrophotometric plate reader. Glucose concentration was determined from a straight-line fit to the concentration of glucose versus the absorbance at 490 nm for the glucose standards.

Figure 10:
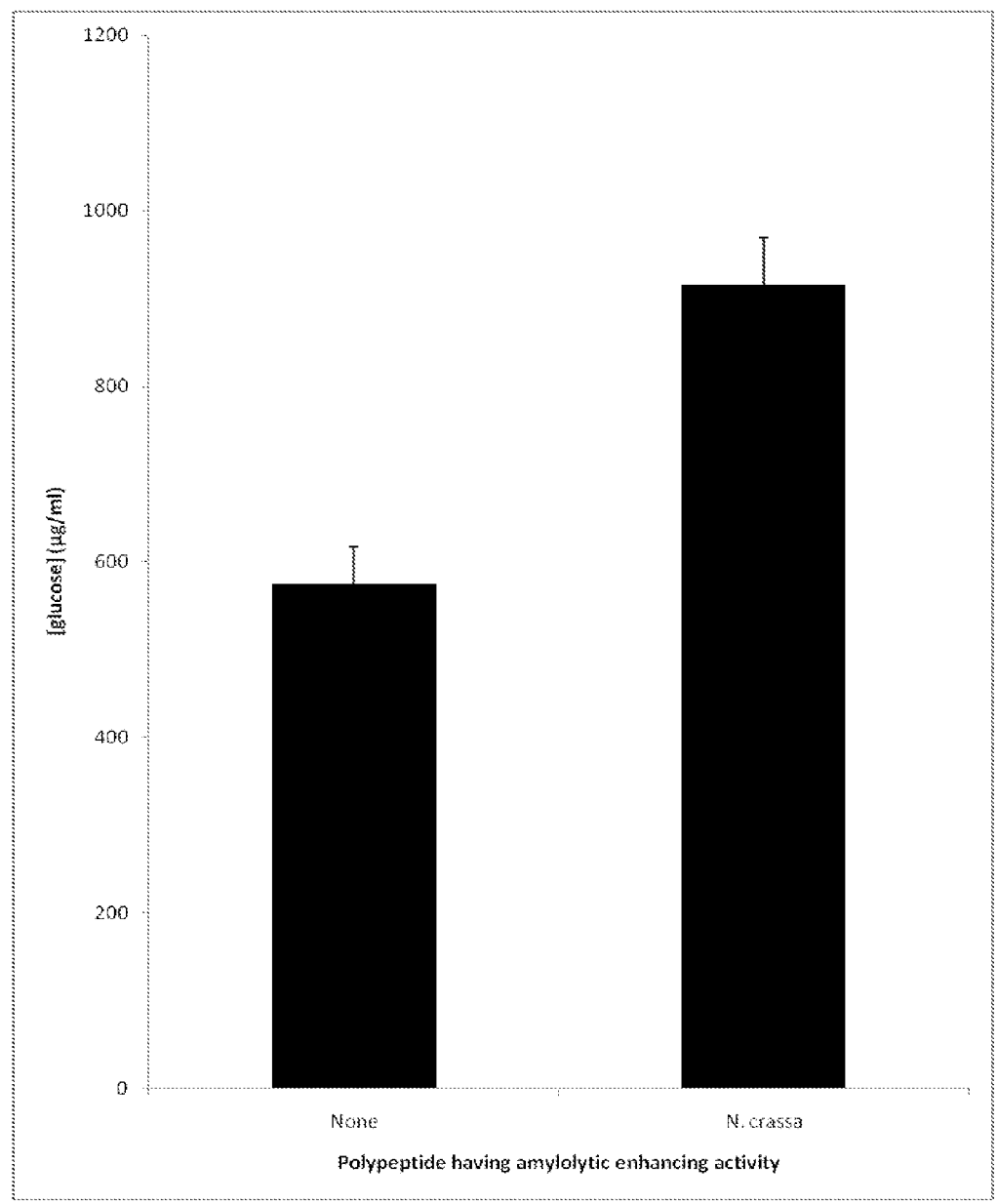
FIG. 10 shows the effect of the *Neurospora crassa* polypeptide having amylolytic enhancing activity on the hydrolysis of corn starch by *Trametes cingulata* amyloglucosidase at pH 5.0 and room temperature.

The results shown in FIG. 10 demonstrated that the polypeptide having amylolytic enhancing activity from *Neurospora crassa* enhanced the hydrolysis of corn starch by *Trametes cingulata* amyloglucosidase.

Example 20

Cloning of an *Aspergillus oryzae* cDNA Sequence of a Gene Encoding a Polypeptide Having Amylolytic Enhancing Activity Cloning and sequencing of the cDNA sequence of a gene encoding an *Aspergillus oryzae* IFO 4177 polypeptide having amylolytic enhancing (aepA) activity was performed as described in WO 2000/56762. The *Aspergillus oryzae* aepA cDNA was subcloned into the *Aspergillus* expression vector pMStr57 (WO 2004/032648) by PCR amplifying the protein coding sequence from the clone NN00055-12-D05-045 with the two synthetic oligonucleotide primers shown below.

```
AoPL2.1:
                                        (SEQ ID NO: 15)
5'-CGAGGATCCAACATAATGAAGGTCTTCG-3'

AoPL2.2:
                                        (SEQ ID NO: 16)
5'-AGCAAGCTTCAGTGACGAAATGCCAT-3'
```

The primers have appropriate restriction sites added to their 5' ends to facilitate sub-cloning of the PCR product. PCR amplification was performed using Extensor Hi-Fidelity PCR Master Mix (ABgene, Surrey, U.K.) following the manufacturer's instructions and using an annealing temperature of 50° C. and an extension temperature of 60° C. and extension time of 1 minute for 20 cycles.

Figure 11:
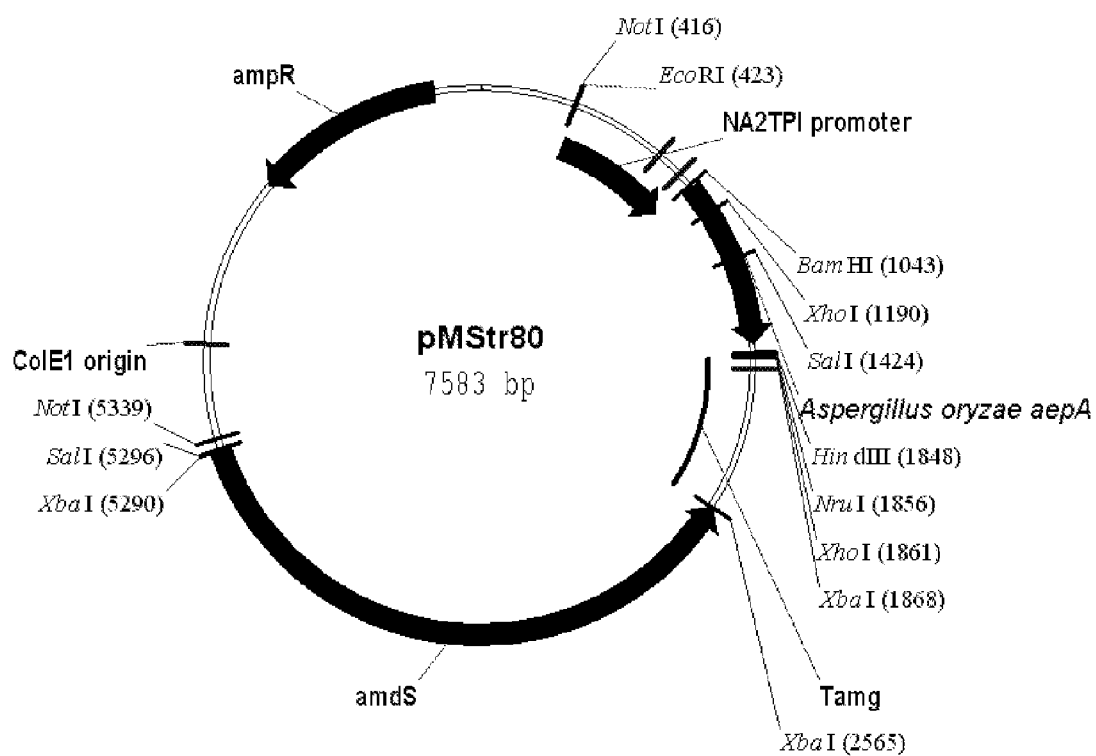
FIG. 11 shows a restriction map of pMStr80.

The PCR fragment was restricted with Bam HI and Hind III and cloned into pMStr57 using standard techniques to produce pMStr80 (FIG. 11).

Example 21

Characterization of Gene Encoding the *Aspergillus oryzae* Polypeptide Having Amylolytic Enhancing Activity The nucleotide sequence (SEQ ID NO: 5) and deduced amino acid sequence (SEQ ID NO: 6) of the cDNA sequence of the *Aspergillus oryzae* gene encoding a polypeptide having amylolytic enhancing (aepA) activity are shown in FIG. 12. The cDNA sequence of 756 bp (including stop codon) encodes a polypeptide of 251 amino acids. The % G+C content of the gene and the mature coding sequence are 55.4% and 55.6%, respectively. Using the SignalP software program (Nielsen et al., 1997, supra), a signal peptide of 18 residues was predicted. The predicted mature protein contains 233 amino acids with a predicted molecular mass of 25.7 kDa and a pI of 4.16.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Aspergillus oryzae* gene encoding the mature polypeptide having amylolytic enhancing activity shared 100% and 99.6% identity (excluding gaps) to the deduced amino acid sequences of two predicted hypothetical polypeptides from *Aspergillus oryzae* and *Aspergillus flavus* (UniProt Accession numbers Q2U8Y3 and B8NDE4, respectively).

Example 22

Construction of *Aspergillus oryzae* MSTR212

*Aspergillus oryzae* strain BECh2 (WO 2000/39322) was transformed with pMStr80 according to Christensen et al., 1988, supra and WO 2004/032648. Twenty transformants were isolated by dilution streaking conidia on amdS selective medium (Christensen et al., 1988, supra) containing 0.01% Triton X-100 to limit colony size and were cultured in 10 ml of YPM medium at 30° C. with shaking at 275 rpm. Samples were taken after 1 and 2 days, and expression of the polypeptide having amylolytic enhancing activity was monitored by SDS-PAGE. Thirteen transformants produced a novel protein band of approximately 34 kDa. Nine of these transformants were again isolated by dilution streaking conidia on the same selective medium containing 0.01% Triton X-100 to limit colony size, and subsequently cultured in 100 ml of YPM medium in baffled 500 ml flasks at 30° C. with shaking at 275 rpm. Samples were taken after 3 days, and expression of the polypeptide having amylolytic enhancing activity was monitored by SDS-PAGE. The highest yielding transformant was selected for further characterization and named *Aspergillus oryzae* MSTR212.

Example 23

Large Shake Flask Cultures of the *Aspergillus oryzae* Polypeptide Having Amylolytic Enhancing Activity Expressed in *Aspergillus oryzae* MSTR212

*Aspergillus oryzae* MSTR212 spores were spread onto a PDA plate and incubated for five days at 34° C. The confluent spore plate was washed twice with 5 ml of 0.01% TWEEN® 20 to maximize the number of spores collected. The spore suspension was then used to inoculate 100 ml of M410 medium per flask in five 500 ml flasks. The culture was incubated at 34° C. with constant shaking at 250 rpm. At day five post-inoculation, the culture broth was collected by filtration through a 0.22 µm EXPRESS™ Plus Membrane. A 5 µl sample of the broth was analyzed by SDS-PAGE as described above to confirm that the protein pattern was of the expected size. Once the broth was shown to contain the expected protein band of 37 kDa by SDS-PAGE, the broth was submitted for purification and evaluation.

Example 24

Purification of *Aspergillus oryzae* Polypeptide Having Amylolytic Enhancing Activity Approximately 250 ml of broth supernatant containing *Aspergillus oryzae* polypeptide having amylolytic enhancing activity, obtained according to Example 23, was desalted by concentrating to 50 ml using an ultrafiltration membrane with a nominal molecular weight cutoff of 10 kDa (Millipore Corporation, Billerica, Mass., USA). Then 250 ml of 20 mM Tris pH 8.5 was added back. The resulting mixture was again concentrated to 50 ml and 250 ml of 20 mM Tris pH 8.5 was again added back. The resulting mixture was then concentrated to 25 ml.

The buffer exchanged sample was purified using a 20 ml MonoQ HIPREP® 16/10 column. A 25 ml volume of the buffer exchanged sample was loaded onto the MonoQ HIPREP® 16/10 column. The column was washed with 2 column volumes of 20 mM Tris pH 8.0 and then eluted using a 20 column volume gradient from 0 to 0.6 M NaCl in 20 mM Tris-HCl pH 8.0. Fractions of 10 ml were collected for the wash step, and fractions of 6 ml were collected from the elution step. Fractions 40 through 54 were submitted to SDS-PAGE analysis. SDS-PAGE on a 8-16% Tris-HCl stain-free gel (Bio-Rad Laboratories, Inc., Hercules, Calif., USA) showed the samples to be greater than 95% pure.

Example 25

Effect of *Aspergillus oryzae* Polypeptide Having Amylolytic Enhancing Activity on the Hydrolysis of Corn Starch

*Aspergillus oryzae* polypeptide having amylolytic enhancing activity was evaluated for its ability to enhance the hydrolysis of corn starch by *Trametes cingulata* amyloglucosidase. Hydrolysis of corn starch was conducted with 5 g of corn starch per liter of 1.75 mM $CaCl_2$-50 mM sodium citrate pH 5.0. *Trametes cingulata* amyloglucosidase, obtained as described in Example 13, was added at 2.0 mg per liter final protein concentration. The hydrolytic reactions were incubated at room temperature overnight with or without 45 mg of *Aspergillus oryzae* polypeptide having amylolytic enhancing activity per liter. For each reaction, a single reaction mixture of 800 µl was prepared and then aliquoted in triplicate at 200 µl per well in an AXYGEN® 1 ml deep well plate. Glucose standards at 1000, 500, 250, 125, 62.5 and 0 mg per liter of 50 mM sodium citrate pH 5.0 buffer were added in duplicate at 200 µl per well. The plate was then sealed with a silicone 96 well plate cap (Nalgene, Rochester, N.Y., USA) and left overnight at room temperature.

After overnight incubation, the plate was assayed for glucose using a glucose oxidase assay. One hundred microliters of 0.5 M NaOH were added to each well of the plate (including glucose standards) to stop the reactions. Then 20 µl from each well were transferred to a clear, flat-bottom 96-well plate containing 200 µl per well liquid glucose oxidase reagent and incubated for 7 minutes at room temperature. The absorbance at 490 nm was then measured using a SPECTRAMAX® 340 pc spectrophotometric plate reader. Glucose concentration was determined from a straight-line fit to the concentration of glucose versus the absorbance at 490 nm for the glucose standards.

Figure 13:
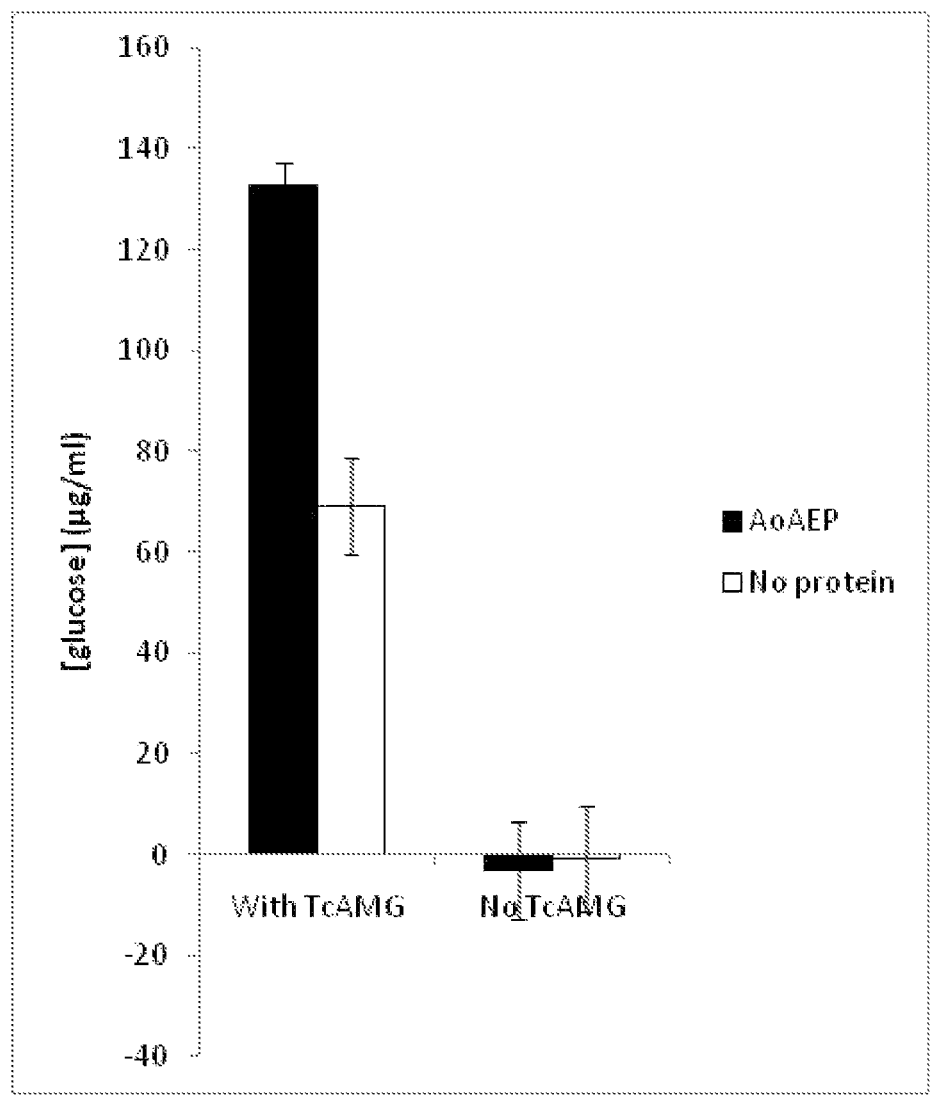
FIG. 13 shows the effect of the *Aspergillus oryzae* polypeptide having amylolytic enhancing activity on the hydrolysis of corn starch by *Trametes cingulata* amyloglucosidase at pH 5.0 and room temperature.

The results shown in FIG. 13 demonstrated that the polypeptide having amylolytic enhancing activity from *Aspergillus oryzae* enhanced the hydrolysis of corn starch by *Trametes cingulata* amyloglucosidase.

The present invention is further described by the following numbered paragraphs:

[1] An isolated polypeptide having amylolytic enhancing activity, selected from the group consisting of:

(a) a polypeptide comprising an amino acid sequence having at least 60% sequence identity to the mature polypeptide of SEQ ID NO: 2, SEQ ID NO: 4, or SEQ ID NO: 6;

(b) a polypeptide encoded by a polynucleotide that hybridizes under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii);

(c) a polypeptide encoded by a polynucleotide comprising a nucleotide sequence having at least 60% sequence identity to the mature polypeptide coding sequence of SEQ ID NO: 1, SEQ ID NO: 3, or SEQ ID NO: 5;

(d) a polypeptide comprising a polypeptide comprising one or more of the motifs selected from the group consisting of N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20); and (e) a variant comprising a substitution, deletion, and/or insertion of one or more (several) amino acids of the mature polypeptide of SEQ ID NO: 2, SEQ ID NO: 4, or SEQ ID NO: 6.

[2] The polypeptide of paragraph 1, comprising an amino acid sequence having at least 60% sequence identity to the mature polypeptide of SEQ ID NO: 2, SEQ ID NO: 4, or SEQ ID NO: 6.

[3] The polypeptide of paragraph 2, comprising an amino acid sequence having at least 65% sequence identity to the mature polypeptide of SEQ ID NO: 2, SEQ ID NO: 4, or SEQ ID NO: 6.

[4] The polypeptide of paragraph 3, comprising an amino acid sequence having at least 70% sequence identity to the mature polypeptide of SEQ ID NO: 2, SEQ ID NO: 4, or SEQ ID NO: 6.

[5] The polypeptide of paragraph 4, comprising an amino acid sequence having at least 75% sequence identity to the mature polypeptide of SEQ ID NO: 2, SEQ ID NO: 4, or SEQ ID NO: 6.

[6] The polypeptide of paragraph 5, comprising an amino acid sequence having at least 80% sequence identity to the mature polypeptide of SEQ ID NO: 2, SEQ ID NO: 4, or SEQ ID NO: 6.

[7] The polypeptide of paragraph 6, comprising an amino acid sequence having at least 85% sequence identity to the mature polypeptide of SEQ ID NO: 2, SEQ ID NO: 4, or SEQ ID NO: 6.

[8] The polypeptide of paragraph 7, comprising an amino acid sequence having at least 90% sequence identity to the mature polypeptide of SEQ ID NO: 2, SEQ ID NO: 4, or SEQ ID NO: 6.

[9] The polypeptide of paragraph 8, comprising an amino acid sequence having at least 95% sequence identity to the mature polypeptide of SEQ ID NO: 2, SEQ ID NO: 4, or SEQ ID NO: 6.

[10] The polypeptide of paragraph 9, comprising an amino acid sequence having at least 97% sequence identity to the mature polypeptide of SEQ ID NO: 2, SEQ ID NO: 4, or SEQ ID NO: 6.

[11] The polypeptide of paragraph 1, comprising or consisting of the amino acid sequence of SEQ ID NO: 2, SEQ ID NO: 4, or SEQ ID NO: 6; or a fragment thereof having amylolytic enhancing activity.

[12] The polypeptide of paragraph 11, comprising or consisting of the amino acid sequence of SEQ ID NO: 2, SEQ ID NO: 4, or SEQ ID NO: 6.

[13] The polypeptide of paragraph 1, comprising or consisting of the mature polypeptide of SEQ ID NO: 2, SEQ ID NO: 4, or SEQ ID NO: 6.

[14] The polypeptide of paragraph 1, which is encoded by a polynucleotide that hybridizes under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii).

[15] The polypeptide of paragraph 14, which is encoded by a polynucleotide that hybridizes under at least medium-high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii).

[16] The polypeptide of paragraph 15, which is encoded by a polynucleotide that hybridizes under at least high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii).

[17] The polypeptide of paragraph 16, which is encoded by a polynucleotide that hybridizes under at least very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii).

[18] The polypeptide of paragraph 1, which is encoded by a polynucleotide comprising a nucleotide sequence having at least 60% sequence identity to the mature polypeptide coding sequence of SEQ ID NO: 1, SEQ ID NO: 3, or SEQ ID NO: 5.

[19] The polypeptide of paragraph 18, which is encoded by a polynucleotide comprising a nucleotide sequence having at least 65% sequence identity to the mature polypeptide coding sequence of SEQ ID NO: 1, SEQ ID NO: 3, or SEQ ID NO: 5.

[20] The polypeptide of paragraph 19, which is encoded by a polynucleotide comprising a nucleotide sequence having at least 70% sequence identity to the mature polypeptide coding sequence of SEQ ID NO: 1, SEQ ID NO: 3, or SEQ ID NO: 5.

[21] The polypeptide of paragraph 20, which is encoded by a polynucleotide comprising a nucleotide sequence having at least 75% sequence identity to the mature polypeptide coding sequence of SEQ ID NO: 1, SEQ ID NO: 3, or SEQ ID NO: 5.

[22] The polypeptide of paragraph 21, which is encoded by a polynucleotide comprising a nucleotide sequence having at least 80% sequence identity to the mature polypeptide coding sequence of SEQ ID NO: 1, SEQ ID NO: 3, or SEQ ID NO: 5.

[23] The polypeptide of paragraph 22, which is encoded by a polynucleotide comprising a nucleotide sequence having at least 85% sequence identity to the mature polypeptide coding sequence of SEQ ID NO: 1, SEQ ID NO: 3, or SEQ ID NO: 5.

[24] The polypeptide of paragraph 23, which is encoded by a polynucleotide comprising a nucleotide sequence having at least 90% sequence identity to the mature polypeptide coding sequence of SEQ ID NO: 1, SEQ ID NO: 3, or SEQ ID NO: 5.

[25] The polypeptide of paragraph 24, which is encoded by a polynucleotide comprising a nucleotide sequence having at least 95% sequence identity to the mature polypeptide coding sequence of SEQ ID NO: 1, SEQ ID NO: 3, or SEQ ID NO: 5.

[26] The polypeptide of paragraph 25, which is encoded by a polynucleotide comprising a nucleotide sequence having at least 97% sequence identity to the mature polypeptide coding sequence of SEQ ID NO: 1, SEQ ID NO: 3, or SEQ ID NO: 5.

[27] The polypeptide of paragraph 1, which is encoded by a polynucleotide comprising or consisting of the nucleotide sequence of SEQ ID NO: 1, SEQ ID NO: 3, or SEQ ID NO: 5; or a subsequence thereof encoding a fragment having amylolytic enhancing activity.

[28] The polypeptide of paragraph 27, which is encoded by a polynucleotide comprising or consisting of the nucleotide sequence of SEQ ID NO: 1, SEQ ID NO: 3, or SEQ ID NO: 5.

[29] The polypeptide of paragraph 1, which is encoded by a polynucleotide comprising or consisting of the mature polypeptide coding sequence of SEQ ID NO: 1, SEQ ID NO: 3, or SEQ ID NO: 5.

[30] The polypeptide of paragraph 1, comprising one or more of the motifs selected from the group consisting of N-G-D-H-G-G-M, Q-T-x-Q-x-Y-L-x-C-A-D, E-K-x-A-A-E-x-C-F, and Y-N-A-R-x(3)-D-Y-N-[FQVP].

[31] The polypeptide of paragraph 1, wherein the polypeptide is a variant comprising a substitution, deletion, and/or insertion of one or more (several) amino acids of the mature polypeptide of SEQ ID NO: 2, SEQ ID NO: 4, or SEQ ID NO: 6.

[32] The polypeptide of any of paragraphs 1-31, wherein the mature polypeptide is amino acids 19 to 385 of SEQ ID NO: 2, amino acids 19 to 385 of SEQ ID NO: 4, or amino acids 19 to 251 of SEQ ID NO: 6.

[33] The polypeptide of any of paragraphs 1-32, wherein the mature polypeptide coding sequence is nucleotides 55 to 1273 of SEQ ID NO: 1, nucleotides 55 to 1214 of SEQ ID NO: 3, or nucleotides 55 to 753 of SEQ ID NO: 5.

[34] An isolated polynucleotide comprising a nucleotide sequence that encodes the polypeptide of any of paragraphs 1-33.

[35] The isolated polynucleotide of paragraph 34, comprising at least one mutation in the mature polypeptide coding sequence of SEQ ID NO: 1, SEQ ID NO: 3, or SEQ ID NO: 5, in which the mutant nucleotide sequence encodes the mature polypeptide of SEQ ID NO: 2, SEQ ID NO: 4, or SEQ ID NO: 6.

[36] A nucleic acid construct comprising the polynucleotide of paragraph 34 or 35 operably linked to one or more (several) control sequences that direct the production of the polypeptide in an expression host.

[37] A recombinant expression vector comprising the polynucleotide of paragraph 34 or 35.

[38] A recombinant host cell comprising the polynucleotide of paragraph 34 or 35 operably linked to one or more (several) control sequences that direct the production of a polypeptide having amylolytic enhancing activity.

[39] A method of producing the polypeptide of any of paragraphs 1-33, comprising: (a) cultivating a cell, which in its wild-type form produces the polypeptide, under conditions conducive for production of the polypeptide; and (b) recovering the polypeptide.

[40] A method of producing the polypeptide of any of paragraphs 1-33, comprising: (a) cultivating a host cell comprising a nucleic acid construct comprising a nucleotide sequence encoding the polypeptide under conditions conducive for production of the polypeptide; and (b) recovering the polypeptide.

[41] A method of producing a mutant of a parent cell, comprising disrupting or deleting a polynucleotide encoding the polypeptide, or a portion thereof, of any of paragraphs 1-33, which results in the mutant producing less of the polypeptide than the parent cell.

[42] A mutant cell produced by the method of paragraph 41.

[43] The mutant cell of paragraph 42, further comprising a gene encoding a native or heterologous protein.

[44] A method of producing a protein, comprising: (a) cultivating the mutant cell of paragraph 43 under conditions conducive for production of the protein; and (b) recovering the protein.

[45] The isolated polynucleotide of paragraph 34 or 35, obtained by (a) hybridizing a population of DNA under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii); and (b) isolating the hybridizing polynucleotide, which encodes a polypeptide having amylolytic enhancing activity.

[46] The isolated polynucleotide of paragraph 45, obtained by (a) hybridizing a population of DNA under at least medium-high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii); and (b) isolating the hybridizing polynucleotide, which encodes a polypeptide having amylolytic enhancing activity.

[47] The isolated polynucleotide of paragraph 46, obtained by (a) hybridizing a population of DNA under at least high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii); and (b) isolating the hybridizing polynucleotide, which encodes a polypeptide having amylolytic enhancing activity.

[48] The isolated polynucleotide of paragraph 47, obtained by (a) hybridizing a population of DNA under at least very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 3 or the genomic DNA sequence comprising the mature polypeptide coding sequence of SEQ ID NO: 5, or (iii) a full-length complementary strand of (i) or (ii); and (b) isolating the hybridizing polynucleotide, which encodes a polypeptide having amylolytic enhancing activity.

[49] The isolated polynucleotide of any of paragraphs 45-48, wherein the mature polypeptide coding sequence is nucleotides 55 to 1273 of SEQ ID NO: 1, nucleotides 55 to 1214 of SEQ ID NO: 3, or nucleotides 55 to 753 of SEQ ID NO: 5.

[50] A method of producing a polynucleotide comprising a mutant nucleotide sequence encoding a polypeptide having amylolytic enhancing activity, comprising: (a) introducing at least one mutation into the mature polypeptide coding sequence of SEQ ID NO: 1, SEQ ID NO: 3, or SEQ ID NO: 5, wherein the mutant nucleotide sequence encodes a polypeptide comprising or consisting of the mature polypeptide of SEQ ID NO: 2, SEQ ID NO: 4, or SEQ ID NO: 6; and (b) recovering the polynucleotide comprising the mutant nucleotide sequence.

[51] A mutant polynucleotide produced by the method of paragraph 50.

[52] A method of producing a polypeptide, comprising: (a) cultivating a cell comprising the mutant polynucleotide of paragraph 51 encoding the polypeptide under conditions conducive for production of the polypeptide; and (b) recovering the polypeptide.

[53] A method of producing the polypeptide of any of paragraphs 1-33, comprising: (a) cultivating a transgenic plant or a plant cell comprising a polynucleotide encoding the polypeptide under conditions conducive for production of the polypeptide; and (b) recovering the polypeptide.

[54] A transgenic plant, plant part or plant cell transformed with a polynucleotide encoding the polypeptide of any of paragraphs 1-33.

[55] A double-stranded inhibitory RNA (dsRNA) molecule comprising a subsequence of the polynucleotide of paragraph 34 or 35, wherein optionally the dsRNA is a siRNA or a miRNA molecule.

[56] The double-stranded inhibitory RNA (dsRNA) molecule of paragraph 55, which is about 15, 16, 17, 18, 19, 20, 21, 22, 23, 24, 25 or more duplex nucleotides in length.

[57] A method of inhibiting the expression of a polypeptide having amylolytic enhancing activity in a cell, comprising administering to the cell or expressing in the cell a double-stranded RNA (dsRNA) molecule, wherein the dsRNA comprises a subsequence of the polynucleotide of paragraph 34 or 35.

[58] The method of paragraph 57, wherein the dsRNA is about 15, 16, 17, 18, 19, 20, 21, 22, 23, 24, 25 or more duplex nucleotides in length.

[59] An isolated polynucleotide encoding a signal peptide comprising or consisting of amino acids 1 to 18 of SEQ ID NO: 2, amino acids 1 to 18 of SEQ ID NO: 4, or amino acids 1 to 18 of SEQ ID NO: 6.

[60] A nucleic acid construct comprising a gene encoding a protein operably linked to the polynucleotide of paragraph 59, wherein the gene is foreign to the polynucleotide encoding the signal peptide.

[61] A recombinant expression vector comprising the polynucleotide of paragraph 59.

[62] A recombinant host cell comprising the polynucleotide of paragraph 59.

[63] A method of producing a protein, comprising: (a) cultivating a recombinant host cell comprising a gene encoding a protein operably linked to the polynucleotide of paragraph 59 under conditions conducive for production of the protein, wherein the gene is foreign to the polynucleotide encoding the signal peptide; and (b) recovering the protein.

[64] A composition comprising the polypeptide of any of paragraphs 1-33.

[65] A detergent composition comprising the polypeptide having amylolytic enhancing activity of any of paragraphs 1-33, one or more (several) amylolytic enzymes, and a surfactant.

[66] A process for degrading a starch-containing material, comprising: treating the starch-containing material with an enzyme composition comprising one or more (several) amylolytic enzymes in the presence of a polypeptide having amylolytic enhancing activity of any of paragraphs 1-33.

[67] The process of paragraph 66, wherein the one or more (several) amylolytic enzymes are selected from the group consisting of an alpha-amylase, a beta-amylase, a maltogenic amylase, an amyloglucoamylase, a pullulanase, and combinations thereof.

[68] The process of paragraph 66 or 67, further comprising recovering the degraded starch-containing material.

[69] The process of paragraph 68, wherein the degraded starch material is glucose, maltose, maltodextrin, or combinations thereof.

[70] The process of any of paragraphs 66-69, wherein the one or more (several) amylolytic enzymes and/or the polypeptide having amylolytic enhancing activity are in the form of a fermentation broth with or without cells.

[71] A process for producing a saccharified product from a starch-containing material, comprising:
(a) liquefying the starch-containing material with an alpha-amylase; and
(b) saccharifying the liquefied starch-containing material with an enzyme composition comprising one or more (several) amylolytic enzymes;
wherein step (a), step (b), or steps (a) and (b); and are conducted in the presence of a polypeptide having amylolytic enhancing activity of any of paragraphs 1-33.

[72] The process of paragraph 71, wherein the one or more (several) amylolytic enzymes are selected from the group consisting of an alpha-amylase, a beta-amylase, a maltogenic amylase, an amyloglucoamylase, a pullulanase, and combinations thereof.

[73] The process of paragraph 71 or 72, further comprising (c) recovering the saccharified product from the saccharified starch-containing material.

[74] The process of paragraph 73, wherein the saccharified product is glucose, maltose, maltodextrin, or combinations thereof.

[75] A process for producing a fermentation product, comprising:
(a) saccharifying a starch-containing material with an enzyme composition comprising one or more (several) amylolytic enzymes in the presence of a polypeptide having amylolytic enhancing activity of any of paragraphs 1-33; and
(b) fermenting the saccharified starch-containing material with one or more (several) fermenting microorganisms to produce a fermentation product.

[76] The process of paragraph 75, further comprising (c) recovering the fermentation product from the fermentation.

[77] The process of paragraph 75 or 76, wherein the one or more (several) amylolytic enzymes are selected from the group consisting of an alpha-amylase, a beta-amylase, a maltogenic amylase, an amyloglucoamylase, a pullulanase, and combinations thereof.

[78] The process of any of paragraphs 75-77, wherein the fermentation product is an alcohol, an organic acid, a ketone, an amino acid, or a gas.

[79] The process of any of paragraphs 75-78, wherein the one or more (several) amylolytic enzymes and/or the polypeptide having amylolytic enhancing activity are in the form of a fermentation broth with or without cells.

[80] The process of any of paragraphs 75-79, wherein steps (a) and (b) are performed simultaneously or sequentially.

[81] A process for producing a fermentation product from a starch-containing material, comprising:
(a) liquefying the starch-containing material with an alpha-amylase;
(b) saccharifying the liquefied starch-containing material with an enzyme composition comprising one or more (several) amylolytic enzymes; and
(c) fermenting the saccharified starch-containing material in the presence of one or more (several) fermenting organisms to produce the fermentation product;
wherein step (a), step (b), or steps (a) and (b) are conducted in the presence of the polypeptide having amylolytic enhancing activity of any of paragraphs 1-33.

[82] The process of paragraph 81, wherein steps (b) and (c) are performed simultaneously or sequentially.

[83] The process of paragraph 81 or 82, wherein the one or more (several) amylolytic enzymes are selected from the group consisting of an alpha-amylase, a beta-amylase, a maltogenic amylase, an amyloglucoamylase, and a pullulanase.

[84] The process of any of paragraphs 81-83, further comprising (d) recovering the fermentation product from the fermentation.

[84] The process of any of paragraphs 81-84, wherein the fermentation product is an alcohol, an organic acid, a ketone, an amino acid, or a gas.

[85] The process of any of paragraphs 81-85, wherein the one or more (several) amylolytic enzymes and/or the polypeptide having amylolytic enhancing activity are in the form of a fermentation broth with or without cells.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for degrading a starch-containing material, comprising: treating the starch-containing material with one or more amylolytic enzymes and a polypeptide having an amino acid sequence having at least 98% sequence identity to the mature polypeptide of SEQ ID NO: 4, wherein the polypeptide has amylolytic enhancing activity.

2. A process for producing a saccharified product from a starch-containing material, comprising:
   (a) liquefying the starch-containing material with an alpha-amylase; and
   (b) saccharifying the liquefied starch-containing material with one or more amylolytic enzymes;
   wherein step (a), step (b), or steps (a) and (b) comprise a polypeptide having an amino acid sequence having at least 98% sequence identity to the mature polypeptide of SEQ ID NO: 4 having amylolytic enhancing activity.

3. A process for producing a fermentation product, comprising:
   (a) saccharifying a starch-containing material with one or more amylolytic enzymes and a
   polypeptide having an amino acid sequence with at least 98% sequence identity to the mature polypeptide of SEQ ID NO: 4 having amylolytic enhancing activity; and
   (b) fermenting the saccharified starch-containing material with one or more fermenting microorganisms to produce the fermentation product.

4. The process of claim 3, further comprising (c) recovering the fermentation product from the fermentation.

5. A process for producing a fermentation product from a starch-containing material, comprising:
   (a) liquefying the starch-containing material with an alpha-amylase;
   (b) saccharifying the liquefied starch-containing material with one or more amylolytic enzymes; and
   (c) fermenting the saccharified starch-containing material in the presence of one or more fermenting organisms to produce the fermentation product;

wherein step (a), step (b), or steps (a) and (b) comprise
a polypeptide comprising an amino acid sequence with at least 98% sequence identity to the mature polypeptide of SEQ ID NO: 4 having amylolytic enhancing activity.

6. The process of claim 5, further comprising (d) recovering the fermentation product from the fermentation.

7. The process of claim 1, wherein the polypeptide comprises an amino acid sequence having at least 99% sequence identity to the mature polypeptide of SEQ ID NO: 4.

8. The process of claim 1, wherein the polypeptide comprises one or more of the motifs selected from the group consisting of N-G-D-H-G-G-M (SEQ ID NO: 17), Q-T-x-Q-x-Y-L-x-C-A-D (SEQ ID NO: 18), E-K-x-A-A-E-x-C-F (SEQ ID NO: 19), and Y-N-A-R-x(3)-D-Y-N-[FQVP] (SEQ ID NO: 20).

* * * * *

SEQUENCE LISTING

<160> NUMBER OF SEQ ID NOS: 20

<210> SEQ ID NO 1
<211> LENGTH: 1276
<212> TYPE: DNA
<213> ORGANISM: Neurospora crassa

<400> SEQUENCE: 1

```
atgaagttct ccatcatctc ggttgccctt gcatcggcca taacggtcga cgcccatgga      60
tatttgacca ttccattcag tcgtacaaga cttggcgcaa aggtaaacaa ataccctgaa     120
gatcgttaga agattgatcg tgctgatttg tgttttctag gccggcttgg acacttgtcc     180
```

```
cgagtgctcc attctggagc ccgtgacggc atggcccaac gttacggaag ccaaggtcgg      240
cagaagcggt ccttgcggct acaatgcccg cgtcagcatc gactacaacc agcctgcgac      300
taactggggt aactctcctg tcgtgacgta cactgccggc gacactgtcg atgtccagtg      360
gtgcgttgac cacaacggcg accacggtgg catgttctcc taccgtatct gccaagacca      420
agagctggtc aacaaattcc tcactcctgg atatctcccg accgaggcgg agaagcaggc      480
tgctgaggat tgcttcgaga agggcaccct tccctgcaca gatgtgaatg gccaatcttg      540
cgacttcagc cctgactgcc agcaaggcca ggcatgctgg aggaacgact ggttcagtaa      600
gttagcctgc atcagtagga agaagcatcc tgctaatcgt cgtgtgactt acttagcctg      660
caacgccttt caagctgaca gccgccgtgg ctgccagggc gtcgacaacg ctgctctcgg      720
atcttgcttc accaccatcg ctggcggcta caccgtcacc aagaagatca agatacccaa      780
ctacatctcc ggccacacct tgctctcctt ccggtggaac tccttccaaa ctgctcaggt      840
ctacctctcg tgcgccgaca tcgccattgt cggcgacagc gcctccacca ccaaagtctc      900
tgccaccgcc acgactcttg tcaccagcag caagactgcc agcgcctctt gcaccccgc       960 cgccaccgtc gctgtgactt caaccacct cgccagcacc agctacggcg agtccatcaa      1020
gatcgttggt tcgatctcgc agctcggcag ctggagcgcc tcgtccggcg ttgccttgtc      1080
tgcgtcgcag tacaccacca gcaacccgct ttggactgcc acggtcagtc tcccggcggg      1140
caccaagttc gagtacaagt tcgtcaaggt gtctagcgaa ggcagtgccg tgacatggga      1200
gagcgatccc aataggtcgt atactgttcc tcagagctgc gctgagtcgg tagctgttga      1260
gtcgtcgtgg aagtag                                                     1276
```

<210> SEQ ID NO 2
<211> LENGTH: 385
<212> TYPE: PRT
<213> ORGANISM: Neurospora crassa

<400> SEQUENCE: 2

```
Met Lys Phe Ser Ile Ile Ser Val Ala Leu Ala Ser Ala Ile Thr Val
1               5                   10                  15

Asp Ala His Gly Tyr Leu Thr Ile Pro Phe Ser Arg Thr Arg Leu Gly
            20                  25                  30

Ala Glu Ala Gly Leu Asp Thr Cys Pro Glu Cys Ser Ile Leu Glu Pro
        35                  40                  45

Val Thr Ala Trp Pro Asn Val Thr Glu Ala Lys Val Gly Arg Ser Gly
    50                  55                  60

Pro Cys Gly Tyr Asn Ala Arg Val Ser Ile Asp Tyr Asn Gln Pro Ala
65                  70                  75                  80

Thr Asn Trp Gly Asn Ser Pro Val Val Thr Tyr Thr Ala Gly Asp Thr
                85                  90                  95

Val Asp Val Gln Trp Cys Val Asp His Asn Gly Asp His Gly Gly Met
            100                 105                 110

Phe Ser Tyr Arg Ile Cys Gln Asp Gln Glu Leu Val Asn Lys Phe Leu
        115                 120                 125

Thr Pro Gly Tyr Leu Pro Thr Glu Ala Glu Lys Gln Ala Ala Glu Asp
    130                 135                 140

Cys Phe Glu Lys Gly Thr Leu Pro Cys Thr Asp Val Asn Gly Gln Ser
145                 150                 155                 160

Cys Asp Phe Ser Pro Asp Cys Gln Gln Gly Gln Ala Cys Trp Arg Asn
                165                 170                 175
```

Asp Trp Phe Thr Cys Asn Ala Phe Gln Ala Asp Ser Arg Arg Gly Cys
            180                 185                 190

Gln Gly Val Asp Asn Ala Ala Leu Gly Ser Cys Phe Thr Thr Ile Ala
        195                 200                 205

Gly Gly Tyr Thr Val Thr Lys Lys Ile Lys Ile Pro Asn Tyr Ile Ser
    210                 215                 220

Gly His Thr Leu Leu Ser Phe Arg Trp Asn Ser Phe Gln Thr Ala Gln
225                 230                 235                 240

Val Tyr Leu Ser Cys Ala Asp Ile Ala Ile Val Gly Asp Ser Ala Ser
                245                 250                 255

Thr Thr Lys Val Ser Ala Thr Ala Thr Thr Leu Val Thr Ser Ser Lys
            260                 265                 270

Thr Ala Ser Ala Ser Cys Thr Pro Ala Ala Thr Val Ala Val Thr Phe
        275                 280                 285

Asn His Leu Ala Ser Thr Ser Tyr Gly Glu Ser Ile Lys Ile Val Gly
    290                 295                 300

Ser Ile Ser Gln Leu Gly Ser Trp Ser Ala Ser Ser Gly Val Ala Leu
305                 310                 315                 320

Ser Ala Ser Gln Tyr Thr Thr Ser Asn Pro Leu Trp Thr Ala Thr Val
                325                 330                 335

Ser Leu Pro Ala Gly Thr Lys Phe Glu Tyr Lys Phe Val Lys Val Ser
            340                 345                 350

Ser Glu Gly Ser Ala Val Thr Trp Glu Ser Asp Pro Asn Arg Ser Tyr
        355                 360                 365

Thr Val Pro Gln Ser Cys Ala Glu Ser Val Ala Val Glu Ser Ser Trp
    370                 375                 380

Lys
385

<210> SEQ ID NO 3
<211> LENGTH: 1217
<212> TYPE: DNA
<213> ORGANISM: Aspergillus nidulans

<400> SEQUENCE: 3
atgaagtctc tcctcgccct tgtggcagga aatctcgtca ctgctgtgtc tggtcatggg      60
tatttgactg tccccgcaag ccgtacccgt ctgggcttcg aggtaagcaa atctcagtct     120
gtttcagtat gcaccaggtt ctaatgcgtg cgtgagtata ggctggaata gatacgtgcc     180
cggaatgctc gatcctcgag ccggtatctg catggccaga tctgactgcg cccaggttg      240 gtagaagtgg tccctgcggt tacaacgctc gggtgagtgt ggattacaat cagcctggag     300
attactgggg aaacgagccg gtggtctcct atactgctgg tgatgtcgtt gaagtacagt     360
ggtgtgtaga ccacaatggg gatcatggtg gaatgtttac atatggtatc tgccagaacc     420
aaaccttggt ggacctgttc ttgacccctg gctatctgcc aacaaacgaa gagaagcaag     480
ctgcagaaga ctgcttctta gaaggtgaac tcagttgcct tcatgtcccc ggacagacct     540
gcaattacaa cccgattgc agtgcaggtg agccatgtta tcaaaacgac tggttcacct     600
gcaatgcttt ccaggcagac aacaatcgcg catgccaagg ggtcgacggg gcagcgttga     660
actcctgcat gaccacgatc gccggtggat acaccgtgac caagaagatc aagatccccg     720
attactcatc cagccatacc ctcctccgat tcagatggaa ttcgttccag acagcccagg     780
tgtatctgca ctgcgctgat attgctattg tgggtggtag tggttcatca cctagcccta     840

```
cttcgaccac atccactgct acctcaacga ctacaccttc ttccaccagc tgcgcgtccg    900
caatctctat accggtgacg ttcaacgcgc ttgttacaac tacctatggt gagaacgtgt    960
accttgccgg atccatcagc cagctaggtt cctggtcgac tagctctgcc gttgctctat   1020
ctgccagcaa atatagttcg tccagcccac tatggaccgt gacagtcgac ctcccagtcg   1080
gggccacatt cgaatacaag tatatcaaga aggagtcgga tggaagtatt gtctgggaga   1140
gtggcccgaa caggagctac actgtgccga ctggctgttc ggggacaacc gccacagaga   1200
gtggtgcatg gcggtag                                                  1217
```

<210> SEQ ID NO 4
<211> LENGTH: 385
<212> TYPE: PRT
<213> ORGANISM: Aspergillus nidulans

<400> SEQUENCE: 4

```
Met Lys Ser Leu Leu Ala Leu Val Ala Gly Asn Leu Val Thr Ala Val
1               5                   10                  15

Ser Gly His Gly Tyr Leu Thr Val Pro Ala Ser Arg Thr Arg Leu Gly
            20                  25                  30

Phe Glu Ala Gly Ile Asp Thr Cys Pro Glu Cys Ser Ile Leu Glu Pro
        35                  40                  45

Val Ser Ala Trp Pro Asp Leu Thr Ala Ala Gln Val Gly Arg Ser Gly
    50                  55                  60

Pro Cys Gly Tyr Asn Ala Arg Val Ser Val Asp Tyr Asn Gln Pro Gly
65                  70                  75                  80

Asp Tyr Trp Gly Asn Glu Pro Val Val Ser Tyr Thr Ala Gly Asp Val
                85                  90                  95

Val Glu Val Gln Trp Cys Val Asp His Asn Gly Asp His Gly Gly Met
            100                 105                 110

Phe Thr Tyr Gly Ile Cys Gln Asn Gln Thr Leu Val Asp Leu Phe Leu
        115                 120                 125

Thr Pro Gly Tyr Leu Pro Thr Asn Glu Glu Lys Gln Ala Ala Glu Asp
    130                 135                 140

Cys Phe Leu Glu Gly Glu Leu Ser Cys Leu His Val Pro Gly Gln Thr
145                 150                 155                 160

Cys Asn Tyr Asn Pro Asp Cys Ser Ala Gly Glu Pro Cys Tyr Gln Asn
                165                 170                 175

Asp Trp Phe Thr Cys Asn Ala Phe Gln Ala Asp Asn Asn Arg Ala Cys
            180                 185                 190

Gln Gly Val Asp Gly Ala Ala Leu Asn Ser Cys Met Thr Thr Ile Ala
        195                 200                 205

Gly Gly Tyr Thr Val Thr Lys Lys Ile Lys Ile Pro Asp Tyr Ser Ser
    210                 215                 220

Ser His Thr Leu Leu Arg Phe Arg Trp Asn Ser Phe Gln Thr Ala Gln
225                 230                 235                 240

Val Tyr Leu His Cys Ala Asp Ile Ala Ile Val Gly Gly Ser Gly Ser
                245                 250                 255

Ser Pro Ser Pro Thr Ser Thr Ser Thr Ala Thr Ser Thr Thr Thr
            260                 265                 270

Pro Ser Ser Thr Ser Cys Ala Ser Ala Ile Ser Ile Pro Val Thr Phe
        275                 280                 285

Asn Ala Leu Val Thr Thr Thr Tyr Gly Glu Asn Val Tyr Leu Ala Gly
    290                 295                 300
```

Ser Ile Ser Gln Leu Gly Ser Trp Ser Thr Ser Ala Val Ala Leu
305                 310                 315                 320

Ser Ala Ser Lys Tyr Ser Ser Ser Pro Leu Trp Thr Val Thr Val
            325                 330                 335

Asp Leu Pro Val Gly Ala Thr Phe Glu Tyr Lys Tyr Ile Lys Lys Glu
            340                 345                 350

Ser Asp Gly Ser Ile Val Trp Glu Ser Gly Pro Asn Arg Ser Tyr Thr
            355                 360                 365

Val Pro Thr Gly Cys Ser Gly Thr Thr Ala Thr Glu Ser Gly Ala Trp
    370                 375                 380

Arg
385

<210> SEQ ID NO 5
<211> LENGTH: 756
<212> TYPE: DNA
<213> ORGANISM: Aspergillus oryzae

<400> SEQUENCE: 5
atgaaggtct tcgccccatt actctccctc agtttagcta cctccgtagc aggccatggc      60
tacatgtaca tcccttctag ccgaacccgt cttggtcacg aggccggtat cgactcatgc     120
cctgagtgtg cgatcctcga gcccgtttcc tcctggccag acctcgatgc ggcaccagtt     180
ggccgcagtg gaccctgcgg ttacaacgcc cgtgacagta tcgactacaa ccagccaacc     240
accaactggg gctccgacgc tgtgcaaagc tacagccccg gcgaagagat cgaagtacag     300
tggtgtgttg accacaacgg tgaccatggt ggcatgttca cgtaccggat ctgtcaagac     360
cagagcattg tcgacaagtt tctcgacccg tcttacctgc ccaccaacga cgagaagcag     420
gctgctgagg attgtttcga cgcaggtctg ctaccctgca cggatgtcag tggccaggag     480
tgtgggtaca gtgcggattg taccgagggc gaggcctgct ggcgtaatga ttggtttacg     540
tgcaatggct tcgaggcttc tgaccggcct aagtgccagg tgttgacaa tgcagagttg      600 aactcctgct ataccagtat tgctggtgga tacacggtga ccaagaaggt caagctgccg     660
gagtacactt ccaaccatac cttgatttcg ttcaagtgga actcgttcca gactggccag     720
atttacctgt cttgtgctga tattgccatt cagtga                              756

<210> SEQ ID NO 6
<211> LENGTH: 251
<212> TYPE: PRT
<213> ORGANISM: Aspergillus oryzae

<400> SEQUENCE: 6

Met Lys Val Phe Ala Pro Leu Leu Ser Leu Ser Leu Ala Thr Ser Val
1               5                   10                  15

Ala Gly His Gly Tyr Met Tyr Ile Pro Ser Ser Arg Thr Arg Leu Gly
            20                  25                  30

His Glu Ala Gly Ile Asp Ser Cys Pro Glu Cys Ala Ile Leu Glu Pro
        35                  40                  45

Val Ser Ser Trp Pro Asp Leu Asp Ala Ala Pro Val Gly Arg Ser Gly
    50                  55                  60

Pro Cys Gly Tyr Asn Ala Arg Asp Ser Ile Asp Tyr Asn Gln Pro Thr
65                  70                  75                  80

Thr Asn Trp Gly Ser Asp Ala Val Gln Ser Tyr Ser Pro Gly Glu Glu
                85                  90                  95

Ile Glu Val Gln Trp Cys Val Asp His Asn Gly Asp His Gly Gly Met

```
            100                 105                 110
Phe Thr Tyr Arg Ile Cys Gln Asp Gln Ser Ile Val Asp Lys Phe Leu
        115                 120                 125

Asp Pro Ser Tyr Leu Pro Thr Asn Asp Glu Lys Gln Ala Ala Glu Asp
130                 135                 140

Cys Phe Asp Ala Gly Leu Leu Pro Cys Thr Asp Val Ser Gly Gln Glu
145                 150                 155                 160

Cys Gly Tyr Ser Ala Asp Cys Thr Glu Gly Glu Ala Cys Trp Arg Asn
                165                 170                 175

Asp Trp Phe Thr Cys Asn Gly Phe Glu Ala Ser Asp Arg Pro Lys Cys
            180                 185                 190

Gln Gly Val Asp Asn Ala Glu Leu Asn Ser Cys Tyr Thr Ser Ile Ala
        195                 200                 205

Gly Gly Tyr Thr Val Thr Lys Lys Val Lys Leu Pro Glu Tyr Thr Ser
    210                 215                 220

Asn His Thr Leu Ile Ser Phe Lys Trp Asn Ser Phe Gln Thr Gly Gln
225                 230                 235                 240

Ile Tyr Leu Ser Cys Ala Asp Ile Ala Ile Gln
                245                 250

<210> SEQ ID NO 7
<211> LENGTH: 36
<212> TYPE: DNA
<213> ORGANISM: Neurospora crassa

<400> SEQUENCE: 7
actggattta ccatgaagtt ctccatcatc tcggtt                         36

<210> SEQ ID NO 8
<211> LENGTH: 38
<212> TYPE: DNA
<213> ORGANISM: Neurospora crassa

<400> SEQUENCE: 8
tcacctctag ttaattaact acttccacga cgactcaa                       38

<210> SEQ ID NO 9
<211> LENGTH: 21
<212> TYPE: DNA
<213> ORGANISM: Neurospora crassa

<400> SEQUENCE: 9
ccacacttct cttccttcct c                                         21

<210> SEQ ID NO 10
<211> LENGTH: 21
<212> TYPE: DNA
<213> ORGANISM: Neurospora crassa

<400> SEQUENCE: 10
ccccatcctt taactatagc g                                         21

<210> SEQ ID NO 11
<211> LENGTH: 36
<212> TYPE: DNA
<213> ORGANISM: Aspergillus nidulans

<400> SEQUENCE: 11
actggattta ccatgaagtc tctcctcgcc cttgtg                         36
```

```
<210> SEQ ID NO 12
<211> LENGTH: 38
<212> TYPE: DNA
<213> ORGANISM: Aspergillus nidulans

<400> SEQUENCE: 12
tcacctctag ttaattaact accgccatgc accactct                              38

<210> SEQ ID NO 13
<211> LENGTH: 33
<212> TYPE: DNA
<213> ORGANISM: Trametes cingulata

<400> SEQUENCE: 13
tttggatcca ccatgcgttt cacgctcctc acc                                   33

<210> SEQ ID NO 14
<211> LENGTH: 30
<212> TYPE: DNA
<213> ORGANISM: Trametes cingulata

<400> SEQUENCE: 14
tttctcgagc taccgccagg tgtcgttctg                                       30

<210> SEQ ID NO 15
<211> LENGTH: 28
<212> TYPE: DNA
<213> ORGANISM: Aspergillus oryzae

<400> SEQUENCE: 15
cgaggatcca acataatgaa ggtcttcg                                         28

<210> SEQ ID NO 16
<211> LENGTH: 26
<212> TYPE: DNA
<213> ORGANISM: Aspergillus oryzae

<400> SEQUENCE: 16
agcaagcttc agtgacgaaa tgccat                                           26

<210> SEQ ID NO 17
<211> LENGTH: 7
<212> TYPE: PRT
<213> ORGANISM: Artificial Sequenc
<220> FEATURE:
<223> OTHER INFORMATION: Artificial Motif Sequence

<400> SEQUENCE: 17

Asn Gly Asp His Gly Gly Met
1               5

<210> SEQ ID NO 18
<211> LENGTH: 11
<212> TYPE: PRT
<213> ORGANISM: Artificial Sequence
<220> FEATURE:
<223> OTHER INFORMATION: Artificial Motif Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
```

```
<221> NAME/KEY: misc_feature
<222> LOCATION: (8)..(8)
<223> OTHER INFORMATION: Xaa can be any naturally occurring amino acid

<400> SEQUENCE: 18

Gln Thr Xaa Gln Xaa Tyr Leu Xaa Cys Ala Asp
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Artificial Motif Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 19

Glu Lys Xaa Ala Ala Glu Xaa Cys Phe
1               5

<210> SEQ ID NO 20
<211> LENGTH: 12
<212> TYPE: PRT
<213> ORGANISM: Artificial Sequence
<220> FEATURE:
<223> OTHER INFORMATION: Artificial Motif Sequence
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa=F, Q, V, P
<220> FEATURE:
<221> NAME/KEY: MISC_FEATURE
<222> LOCATION: (12)..(12)
<223> OTHER INFORMATION: X=F, Q, V, P

<400> SEQUENCE: 20

Tyr Asn Ala Arg Xaa Xaa Xaa Xaa Asp Tyr Asn Xaa
1               5                   10
```